(12) United States Patent
Igov

(10) Patent No.: US 9,138,207 B2
(45) Date of Patent: Sep. 22, 2015

(54) METHODS AND DEVICES FOR LAPAROSCOPIC SURGERY

(75) Inventor: Igor Igov, Lod (IL)

(73) Assignee: TELEFLEX MEDICAL INCORPORATED, Morrisville, NC (US)

(*) Notice: Subject to any disclaimer, the term of this patent is extended or adjusted under 35 U.S.C. 154(b) by 942 days.

(21) Appl. No.: 12/781,831

(22) Filed: May 18, 2010

(65) Prior Publication Data

US 2010/0298774 A1 Nov. 25, 2010

Related U.S. Application Data

(60) Provisional application No. 61/179,413, filed on May 19, 2009.

(51) Int. Cl.
| | |
|---|---|
| *A61B 17/00* | (2006.01) |
| *A61B 17/29* | (2006.01) |
| *A61B 18/14* | (2006.01) |
| *A61B 19/00* | (2006.01) |
| *A61B 17/04* | (2006.01) |
| *A61B 17/30* | (2006.01) |

(52) U.S. Cl.
CPC ......... *A61B 17/00234* (2013.01); *A61B 17/29* (2013.01); *A61B 18/1445* (2013.01); *A61B 19/26* (2013.01); *A61B 2017/00287* (2013.01); *A61B 2017/00464* (2013.01); *A61B 2017/0479* (2013.01); *A61B 2017/2931* (2013.01); *A61B 2017/2939* (2013.01); *A61B 2017/306* (2013.01)

(58) Field of Classification Search
CPC ............. A61B 17/00234; A61B 17/29; A61B 2017/00283; A61B 2017/00464; A61B 2017/2931

USPC ...................................... 606/1, 108, 205–207
See application file for complete search history.

(56) References Cited

U.S. PATENT DOCUMENTS

| | | | |
|---|---|---|---|
| 4,177,814 A | 12/1979 | Knepshield et al. |
| 4,424,833 A | 1/1984 | Spector et al. |
| 4,453,928 A | 6/1984 | Steiger |
| 4,655,752 A | 4/1987 | Honkanen et al. |
| 4,746,975 A | 5/1988 | Ogiu |
| 4,831,444 A | 5/1989 | Kato |
| 4,929,235 A | 5/1990 | Merry et al. |
| 4,943,280 A | 7/1990 | Lander |
| 4,944,732 A | 7/1990 | Russo |
| 4,960,412 A | 10/1990 | Fink |
| 4,978,341 A | 12/1990 | Niederhauser |
| 5,015,250 A | 5/1991 | Foster |
| 5,092,846 A | 3/1992 | Nishijima et al. |
| 5,112,310 A | 5/1992 | Grobe |

(Continued)

FOREIGN PATENT DOCUMENTS

| | | |
|---|---|---|
| EP | 1515665 B1 | 2/2012 |
| WO | WO9308867 A3 | 6/1993 |

(Continued)

*Primary Examiner* — Katherine Rodjom
(74) *Attorney, Agent, or Firm* — Baker and Hostetler LLP

(57) ABSTRACT

Two part laparoscopic tools and surgical methods using such tools are presented. The tools and methods enable use of multiple surgical tools each having wide tool heads to be used in a body cavity using a single wide trocar and one or more narrow incisions, thereby reducing surgical risk and enhancing patient comfort and shortening recovery time. Additional instruments for facilitating laparoscopic surgery are also presented.

11 Claims, 24 Drawing Sheets

(56) References Cited

U.S. PATENT DOCUMENTS

| | | | |
|---|---|---|---|
| 5,127,626 A | 7/1992 | Hilal | |
| 5,152,749 A | 10/1992 | Giesy et al. | |
| 5,167,627 A | 12/1992 | Clegg et al. | |
| 5,180,373 A | 1/1993 | Green et al. | |
| 5,197,955 A | 3/1993 | Stephens et al. | |
| 5,209,736 A | 5/1993 | Stephens et al. | |
| 5,211,370 A | 5/1993 | Powers | |
| 5,226,891 A | 7/1993 | Bushatz et al. | |
| 5,242,412 A | 9/1993 | Blake, III | |
| 5,250,075 A * | 10/1993 | Badie | 606/207 |
| 5,295,994 A | 3/1994 | Bonutti | |
| 5,308,336 A | 5/1994 | Hart et al. | |
| 5,312,363 A | 5/1994 | Ryan et al. | |
| 5,330,437 A | 7/1994 | Durman | |
| 5,342,315 A | 8/1994 | Rowe et al. | |
| 5,352,219 A | 10/1994 | Reddy | |
| 5,376,077 A | 12/1994 | Gomringer | |
| 5,389,077 A | 2/1995 | Melinyshyn et al. | |
| 5,395,342 A | 3/1995 | Yoon | |
| 5,401,248 A | 3/1995 | Bencini | |
| 5,441,059 A * | 8/1995 | Dannan | 128/898 |
| 5,476,475 A | 12/1995 | Gadberry | |
| 5,545,179 A | 8/1996 | Williamson, IV | |
| 5,569,183 A | 10/1996 | Kieturakis | |
| 5,593,402 A * | 1/1997 | Patrick | 606/1 |
| 5,634,911 A | 6/1997 | Hermann et al. | |
| 5,658,306 A * | 8/1997 | Kieturakis et al. | 606/184 |
| 5,707,359 A | 1/1998 | Bufalini | |
| 5,755,713 A | 5/1998 | Bilof et al. | |
| 5,792,113 A | 8/1998 | Kramer et al. | |
| 5,827,228 A | 10/1998 | Rowe | |
| 5,871,474 A | 2/1999 | Hermann et al. | |
| 5,882,344 A | 3/1999 | Stouder, Jr. | |
| 5,895,377 A | 4/1999 | Smith et al. | |
| 5,896,166 A | 4/1999 | D'Alfonso et al. | |
| 5,976,146 A | 11/1999 | Ogawa et al. | |
| 5,979,452 A | 11/1999 | Fogarty et al. | |
| 5,980,455 A | 11/1999 | Daniel et al. | |
| 5,989,240 A | 11/1999 | Strowe | |
| 6,004,303 A | 12/1999 | Peterson | |
| 6,095,970 A | 8/2000 | Hidaka et al. | |
| 6,106,511 A | 8/2000 | Jensen | |
| 6,159,200 A | 12/2000 | Verdura et al. | |
| 6,165,184 A | 12/2000 | Verdura et al. | |
| 6,187,000 B1 | 2/2001 | Davison et al. | |
| 6,258,065 B1 | 7/2001 | Dennis et al. | |
| 6,287,280 B1 | 9/2001 | Lampropoulos et al. | |
| 6,309,345 B1 | 10/2001 | Stelzer et al. | |
| 6,309,397 B1 | 10/2001 | Julian et al. | |
| 6,312,435 B1 | 11/2001 | Wallace et al. | |
| 6,436,107 B1 | 8/2002 | Wang et al. | |
| 6,443,159 B1 | 9/2002 | Fogarty et al. | |
| 6,447,489 B1 | 9/2002 | Peterson | |
| 6,569,120 B1 | 5/2003 | Green et al. | |
| 6,602,240 B2 | 8/2003 | Hermann et al. | |
| 6,608,639 B2 | 8/2003 | McGovern | |
| 6,645,196 B1 | 11/2003 | Nixon et al. | |
| 6,723,043 B2 | 4/2004 | Kleeman et al. | |
| 6,752,827 B2 | 6/2004 | Ross et al. | |
| 6,802,836 B2 | 10/2004 | Bouphavichith et al. | |
| 6,860,869 B2 | 3/2005 | Dennis | |
| 6,918,871 B2 | 7/2005 | Schulze | |
| 6,963,792 B1 | 11/2005 | Green | |
| 7,018,384 B2 | 3/2006 | Skakoon | |
| 7,041,083 B2 | 5/2006 | Chu et al. | |
| 7,044,937 B1 | 5/2006 | Kirwan et al. | |
| 7,056,303 B2 | 6/2006 | Dennis et al. | |
| 7,083,626 B2 | 8/2006 | Brustad et al. | |
| 7,125,403 B2 | 10/2006 | Julian et al. | |
| 7,163,525 B2 | 1/2007 | Franer | |
| 7,226,411 B2 | 6/2007 | Akiba | |
| 7,235,062 B2 | 6/2007 | Brustad | |
| 7,297,141 B2 | 11/2007 | Kathrani et al. | |
| 7,300,397 B2 | 11/2007 | Adler et al. | |
| 7,331,967 B2 | 2/2008 | Lee et al. | |
| 7,341,587 B2 | 3/2008 | Molz, IV et al. | |
| 7,367,973 B2 | 5/2008 | Manzo et al. | |
| 7,371,227 B2 | 5/2008 | Zeiner | |
| 7,390,317 B2 | 6/2008 | Taylor et al. | |
| 7,438,702 B2 | 10/2008 | Hart et al. | |
| 7,473,221 B2 | 1/2009 | Ewers et al. | |
| 7,481,765 B2 | 1/2009 | Ewers et al. | |
| 7,494,460 B2 | 2/2009 | Haarstad et al. | |
| 7,559,887 B2 | 7/2009 | Dannan | |
| 7,563,250 B2 | 7/2009 | Wenchell | |
| 7,641,648 B2 | 1/2010 | Bouphavichith et al. | |
| 7,651,478 B2 | 1/2010 | Brustad | |
| 7,666,181 B2 * | 2/2010 | Abou El Kheir | 606/1 |
| 7,691,103 B2 | 4/2010 | Fernandez et al. | |
| 7,717,878 B2 | 5/2010 | Smith | |
| 7,722,599 B2 | 5/2010 | Julian et al. | |
| 7,753,901 B2 | 7/2010 | Piskun et al. | |
| 7,753,928 B2 | 7/2010 | de la Torre et al. | |
| 7,758,569 B2 | 7/2010 | Brock | |
| 7,779,716 B2 | 8/2010 | Dellach et al. | |
| 7,803,135 B2 | 9/2010 | Franer | |
| 7,828,775 B2 | 11/2010 | Okoniewski | |
| 7,828,808 B2 | 11/2010 | Hinman et al. | |
| 7,833,275 B2 | 11/2010 | Mears et al. | |
| 7,857,754 B2 | 12/2010 | Spivey et al. | |
| 7,862,553 B2 | 1/2011 | Ewaschuk | |
| 7,883,493 B2 | 2/2011 | Brustad | |
| 7,918,376 B1 | 4/2011 | Knodel et al. | |
| 7,918,826 B2 | 4/2011 | Armstrong et al. | |
| 7,918,827 B2 | 4/2011 | Smith | |
| 7,935,130 B2 | 5/2011 | Williams | |
| 7,972,307 B2 | 7/2011 | Kraus et al. | |
| 7,976,501 B2 | 7/2011 | Franer et al. | |
| 7,988,671 B2 | 8/2011 | Albrecht et al. | |
| 8,002,764 B2 | 8/2011 | High | |
| 8,007,472 B2 | 8/2011 | Exline et al. | |
| 8,007,492 B2 | 8/2011 | Dipoto et al. | |
| 8,012,160 B2 | 9/2011 | Jensen et al. | |
| 8,016,755 B2 | 9/2011 | Ewers et al. | |
| 8,021,358 B2 | 9/2011 | Doyle et al. | |
| 8,029,475 B2 | 10/2011 | Franer et al. | |
| 8,033,995 B2 | 10/2011 | Cropper et al. | |
| 8,070,676 B2 | 12/2011 | Ewers et al. | |
| 8,075,477 B2 | 12/2011 | Nakamura et al. | |
| 8,075,530 B2 | 12/2011 | Taylor et al. | |
| 8,088,062 B2 | 1/2012 | Zwolinski | |
| 8,092,432 B2 | 1/2012 | Nordgren | |
| 8,097,000 B2 | 1/2012 | Albrecht | |
| 8,100,929 B2 | 1/2012 | Franer et al. | |
| 8,105,234 B2 | 1/2012 | Ewers et al. | |
| 8,109,910 B2 | 2/2012 | Zastawny et al. | |
| 8,133,254 B2 | 3/2012 | Dumbauld et al. | |
| 8,147,457 B2 | 4/2012 | Michael et al. | |
| 8,152,773 B2 | 4/2012 | Albrecht et al. | |
| 8,152,774 B2 | 4/2012 | Pasqualucci | |
| 8,172,806 B2 | 5/2012 | Smith | |
| 8,192,405 B2 | 6/2012 | Racenet et al. | |
| 8,225,798 B2 | 7/2012 | Baldwin et al. | |
| 8,348,828 B2 | 1/2013 | Asada et al. | |
| 8,353,487 B2 | 1/2013 | Trusty et al. | |
| 8,353,897 B2 | 1/2013 | Doyle et al. | |
| 8,376,938 B2 | 2/2013 | Morgan et al. | |
| 8,377,044 B2 | 2/2013 | Coe et al. | |
| 8,409,172 B2 | 4/2013 | Moll et al. | |
| 8,423,182 B2 | 4/2013 | Robinson et al. | |
| 8,425,406 B2 | 4/2013 | Smith et al. | |
| 8,430,851 B2 | 4/2013 | McGinley et al. | |
| 8,444,631 B2 | 5/2013 | Yeung et al. | |
| 8,458,896 B2 | 6/2013 | Chandrasekaran et al. | |
| 8,475,359 B2 | 7/2013 | Asada et al. | |
| 8,506,555 B2 | 8/2013 | Ruiz Morales | |
| 2003/0004529 A1 | 1/2003 | Tsonton et al. | |
| 2003/0041865 A1 | 3/2003 | Mollenauer | |
| 2003/0130693 A1 | 7/2003 | Levin et al. | |
| 2004/0181150 A1 | 9/2004 | Evans et al. | |
| 2004/0260246 A1 | 12/2004 | Desmond | |
| 2005/0015103 A1 | 1/2005 | Popov | |
| 2005/0096507 A1 | 5/2005 | Prosek | |
| 2005/0131349 A1 | 6/2005 | Albrecht et al. | |

(56) References Cited

U.S. PATENT DOCUMENTS

| | | |
|---|---|---|
| 2005/0203543 A1 | 9/2005 | Hilal et al. |
| 2006/0200185 A1 | 9/2006 | Marchek et al. |
| 2006/0276835 A1 | 12/2006 | Uchida |
| 2007/0027447 A1 | 2/2007 | Theroux et al. |
| 2007/0179507 A1 | 8/2007 | Shah |
| 2007/0182842 A1 | 8/2007 | Sonnenschein et al. |
| 2007/0255257 A1 | 11/2007 | Willis et al. |
| 2007/0296827 A1 | 12/2007 | Kubota et al. |
| 2008/0015552 A1* | 1/2008 | Doyle et al. ............ 606/1 |
| 2008/0183153 A1 | 7/2008 | Enns |
| 2008/0228213 A1 | 9/2008 | Blakeney et al. |
| 2008/0242939 A1 | 10/2008 | Johnston |
| 2008/0249475 A1 | 10/2008 | Albrecht et al. |
| 2008/0249558 A1 | 10/2008 | Cahill |
| 2008/0262302 A1 | 10/2008 | Azarbarzin et al. |
| 2008/0309758 A1 | 12/2008 | Karasawa et al. |
| 2009/0024163 A1 | 1/2009 | Zeiner et al. |
| 2009/0082627 A1 | 3/2009 | Karasawa et al. |
| 2009/0082634 A1 | 3/2009 | Kathrani et al. |
| 2009/0131754 A1 | 5/2009 | Ewers et al. |
| 2009/0192344 A1 | 7/2009 | Bakos et al. |
| 2009/0209947 A1* | 8/2009 | Gordin et al. ............ 606/1 |
| 2009/0254050 A1 | 10/2009 | Bottcher |
| 2009/0259141 A1 | 10/2009 | Ewers et al. |
| 2009/0270676 A1 | 10/2009 | Sicvol |
| 2009/0270679 A1 | 10/2009 | Hoeg et al. |
| 2009/0270685 A1 | 10/2009 | Moreno et al. |
| 2009/0270818 A1 | 10/2009 | Duke |
| 2009/0287045 A1 | 11/2009 | Mitelberg et al. |
| 2009/0299135 A1 | 12/2009 | Spivey |
| 2010/0010501 A2 | 1/2010 | Sipilä et al. |
| 2010/0057110 A1 | 3/2010 | Lampropoulos et al. |
| 2010/0063437 A1 | 3/2010 | Nelson et al. |
| 2010/0081883 A1 | 4/2010 | Murray et al. |
| 2010/0125164 A1 | 5/2010 | LaBombard |
| 2010/0191050 A1 | 7/2010 | Zwolinski |
| 2010/0191255 A1 | 7/2010 | Crainich et al. |
| 2010/0241136 A1 | 9/2010 | Doyle et al. |
| 2010/0249700 A1 | 9/2010 | Spivey |
| 2010/0268028 A1 | 10/2010 | Ghabrial |
| 2010/0280326 A1 | 11/2010 | Hess et al. |
| 2010/0331856 A1 | 12/2010 | Carlson et al. |
| 2011/0028794 A1 | 2/2011 | Widenhouse et al. |
| 2011/0066000 A1 | 3/2011 | Ibrahim et al. |
| 2011/0077460 A1 | 3/2011 | Hashiba et al. |
| 2011/0087266 A1 | 4/2011 | Conlon et al. |
| 2011/0124960 A1 | 5/2011 | St. Onge et al. |
| 2011/0124961 A1 | 5/2011 | Zimmon |
| 2011/0130787 A1 | 6/2011 | Cinquin et al. |
| 2011/0152615 A1 | 6/2011 | Schostek et al. |
| 2011/0230723 A1 | 9/2011 | Castro et al. |
| 2011/0237890 A1 | 9/2011 | Farritor et al. |
| 2011/0276038 A1 | 11/2011 | McIntyre et al. |
| 2011/0277775 A1 | 11/2011 | Holop et al. |
| 2011/0288573 A1 | 11/2011 | Yates et al. |
| 2011/0290854 A1 | 12/2011 | Timm et al. |
| 2012/0083826 A1 | 4/2012 | Chao et al. |

FOREIGN PATENT DOCUMENTS

| | | |
|---|---|---|
| WO | 9407552 A1 | 4/1994 |
| WO | WO9413335 A1 | 6/1994 |
| WO | 9426179 A1 | 11/1994 |
| WO | WO9530374 A1 | 11/1995 |
| WO | WO9632889 A1 | 10/1996 |
| WO | WO9840016 A3 | 10/1998 |
| WO | WO9853865 A1 | 12/1998 |
| WO | WO9935971 A1 | 7/1999 |
| WO | 0207618 A1 | 1/2002 |
| WO | 03015848 A1 | 2/2003 |
| WO | WO03013367 A3 | 7/2003 |
| WO | WO03059412 A3 | 11/2003 |
| WO | WO2004043267 A3 | 9/2004 |
| WO | WO2005086564 A3 | 3/2006 |
| WO | WO2005112799 A8 | 8/2006 |
| WO | WO2006118650 A1 | 11/2006 |
| WO | WO2004066828 A3 | 12/2006 |
| WO | 2007073931 A1 | 7/2007 |
| WO | WO2007088206 A3 | 9/2007 |
| WO | 2010114634 A1 | 10/2007 |
| WO | WO2007111571 A1 | 10/2007 |
| WO | WO2007136829 A1 | 11/2007 |
| WO | WO2007119060 A3 | 12/2007 |
| WO | WO2008005433 A1 | 1/2008 |
| WO | WO2008029109 A1 | 3/2008 |
| WO | WO2008057117 A1 | 5/2008 |
| WO | WO2008045744 A3 | 7/2008 |
| WO | 2007008332 A3 | 10/2008 |
| WO | WO2008121259 A3 | 12/2008 |
| WO | WO2009147669 A1 | 12/2009 |
| WO | 2010098871 A3 | 2/2010 |
| WO | 2010044051 A1 | 4/2010 |
| WO | 2010060436 A1 | 6/2010 |
| WO | 2010081482 A1 | 7/2010 |
| WO | WO2010111319 A1 | 9/2010 |
| WO | WO2010136805 A1 | 12/2010 |
| WO | WO2011056458 A1 | 5/2011 |
| WO | WO2011140444 A1 | 11/2011 |

* cited by examiner

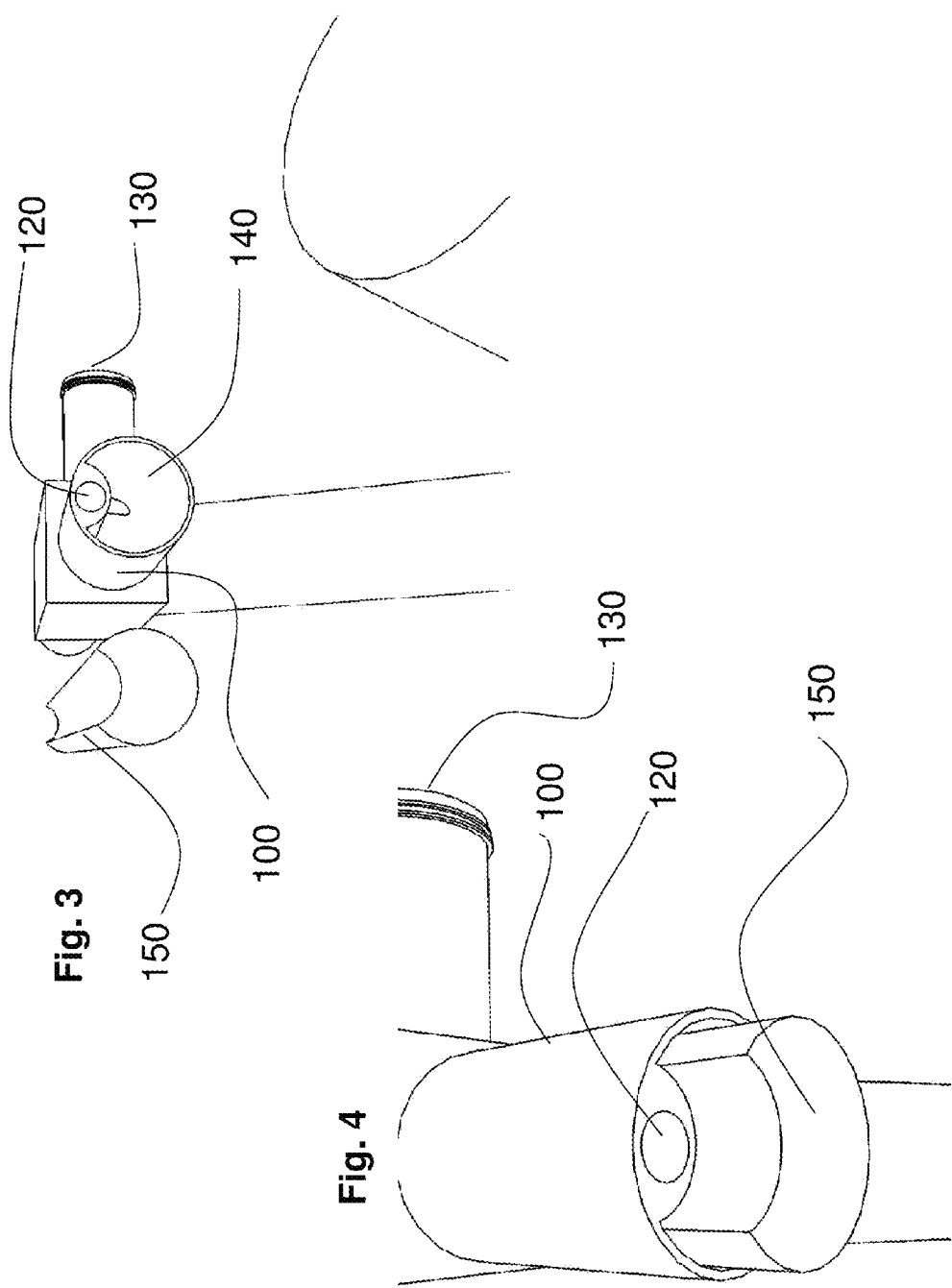

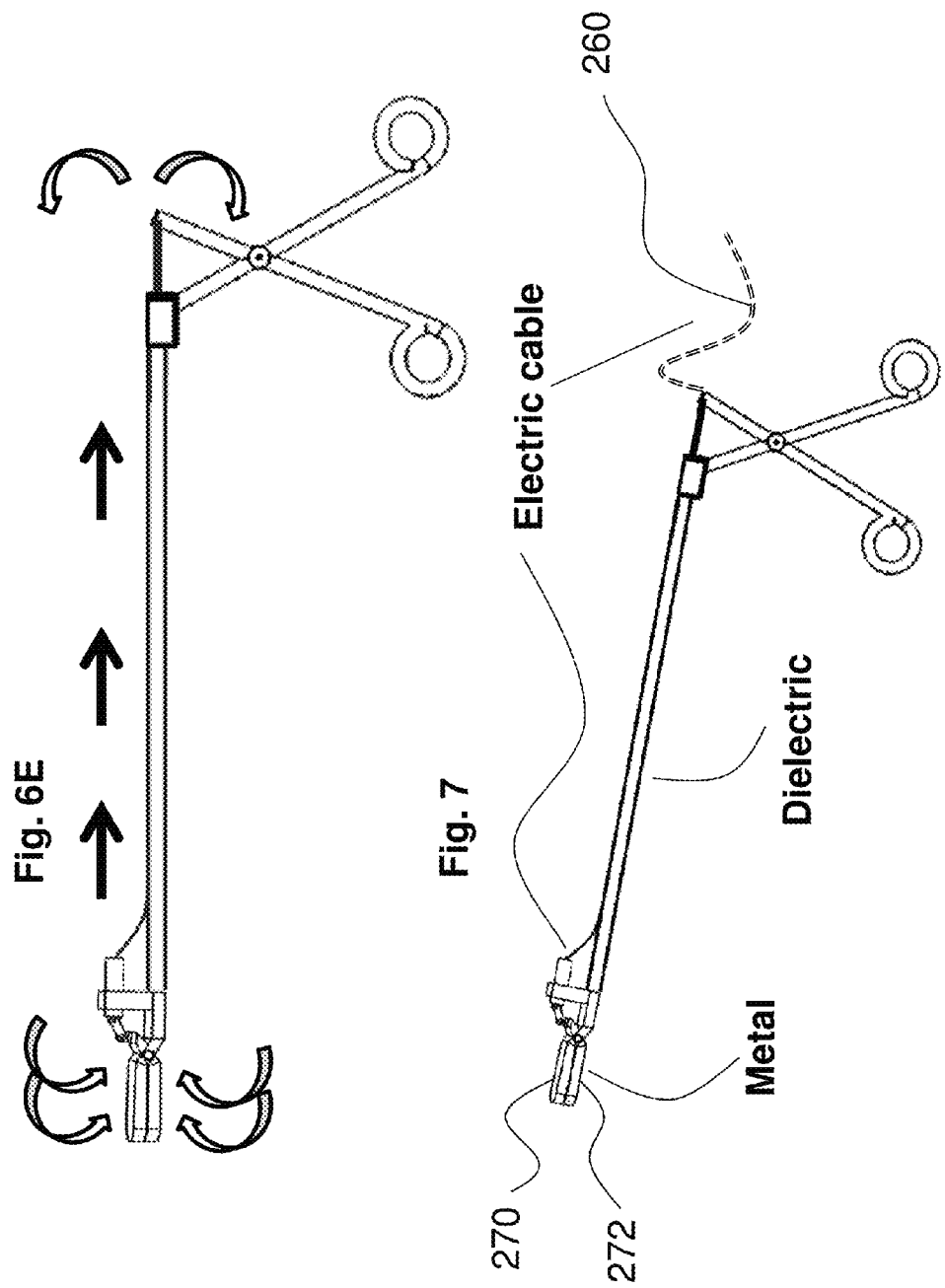

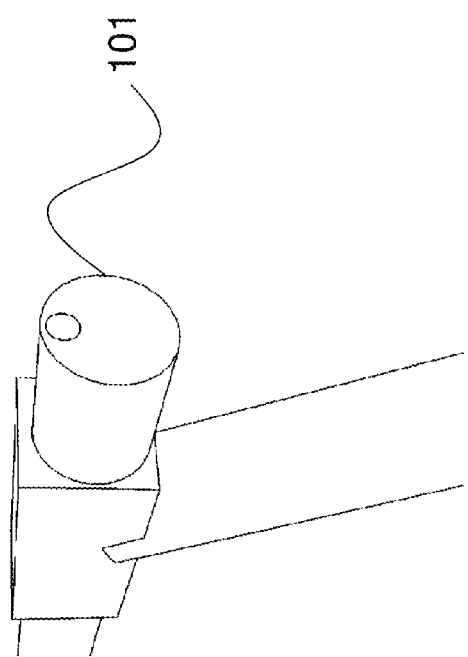
Fig. 8
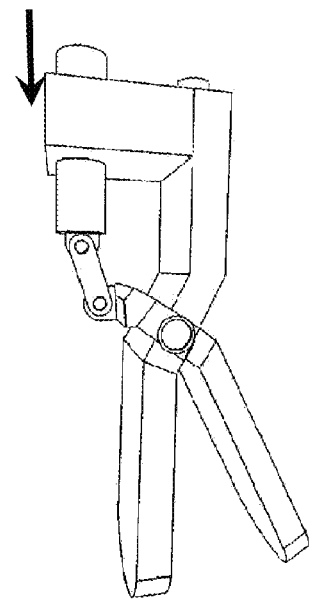
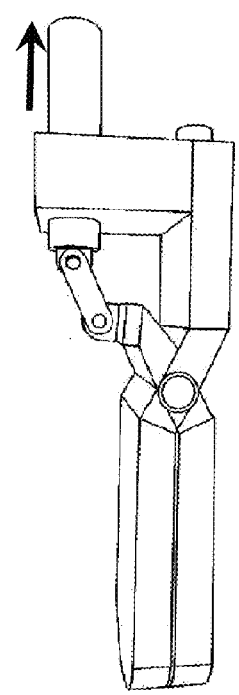
Fig. 9

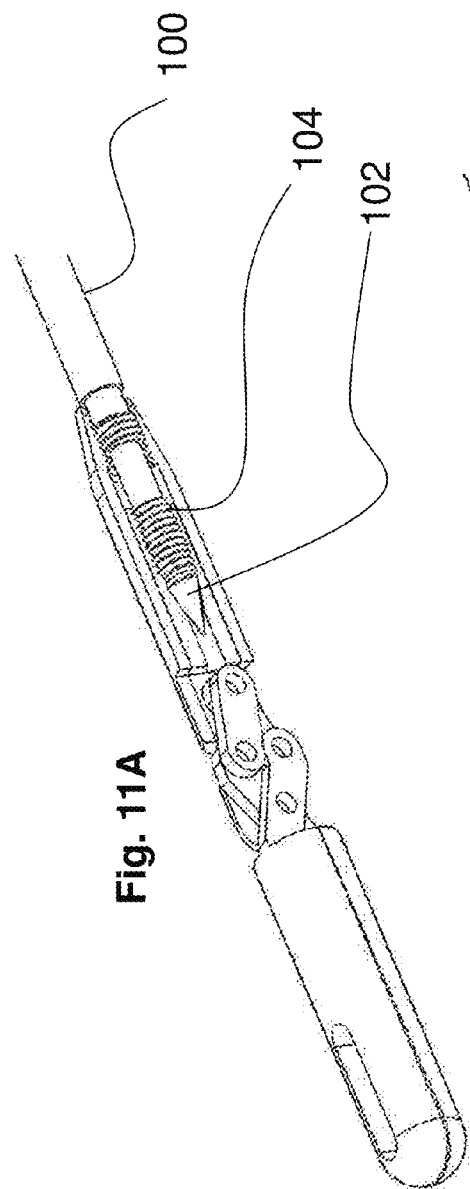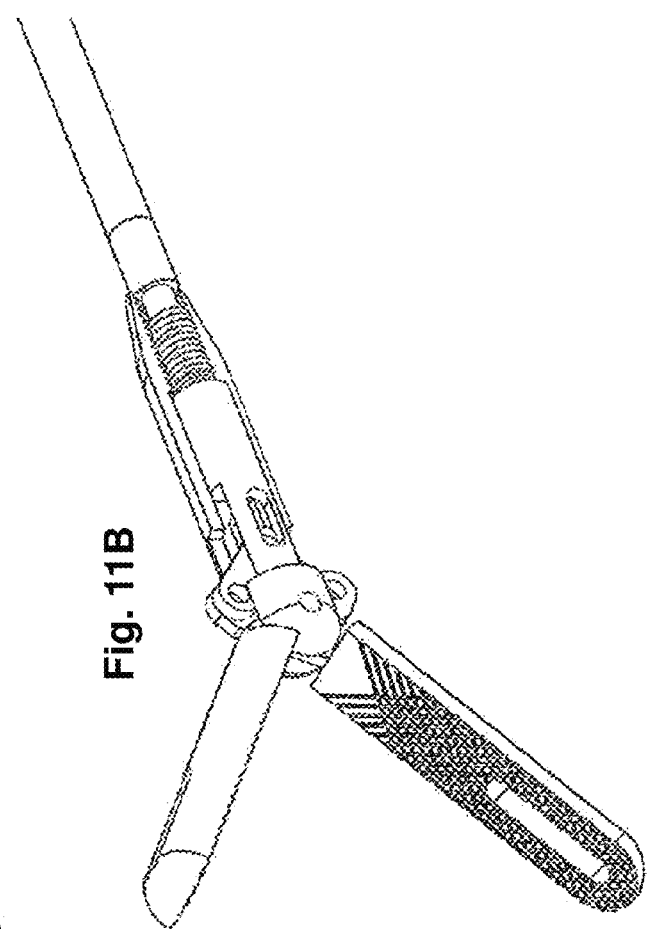

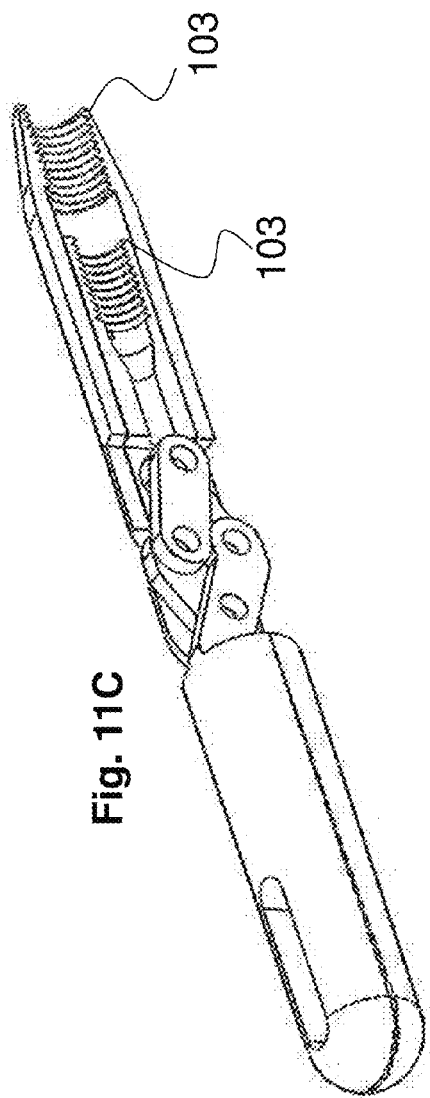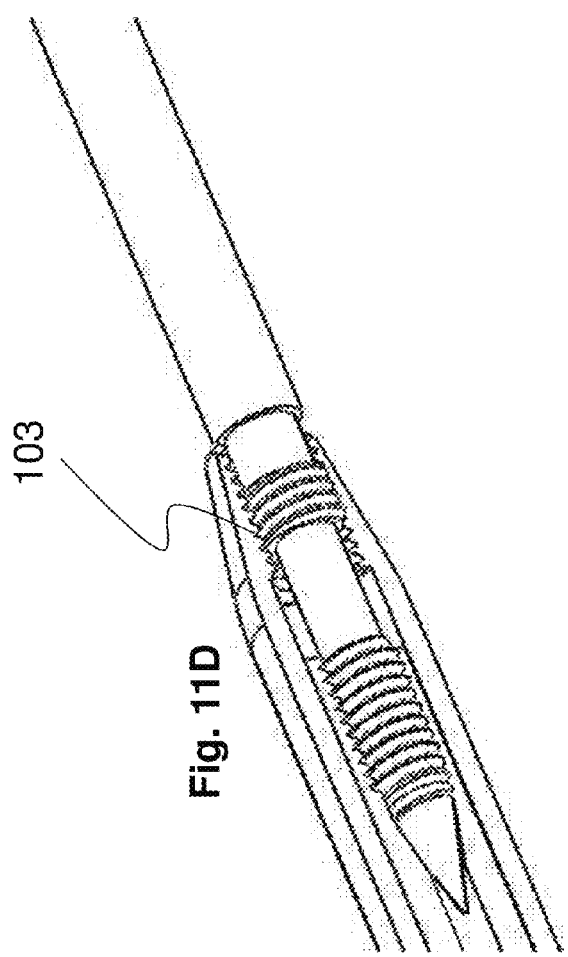
Fig. 11C
Fig. 11D

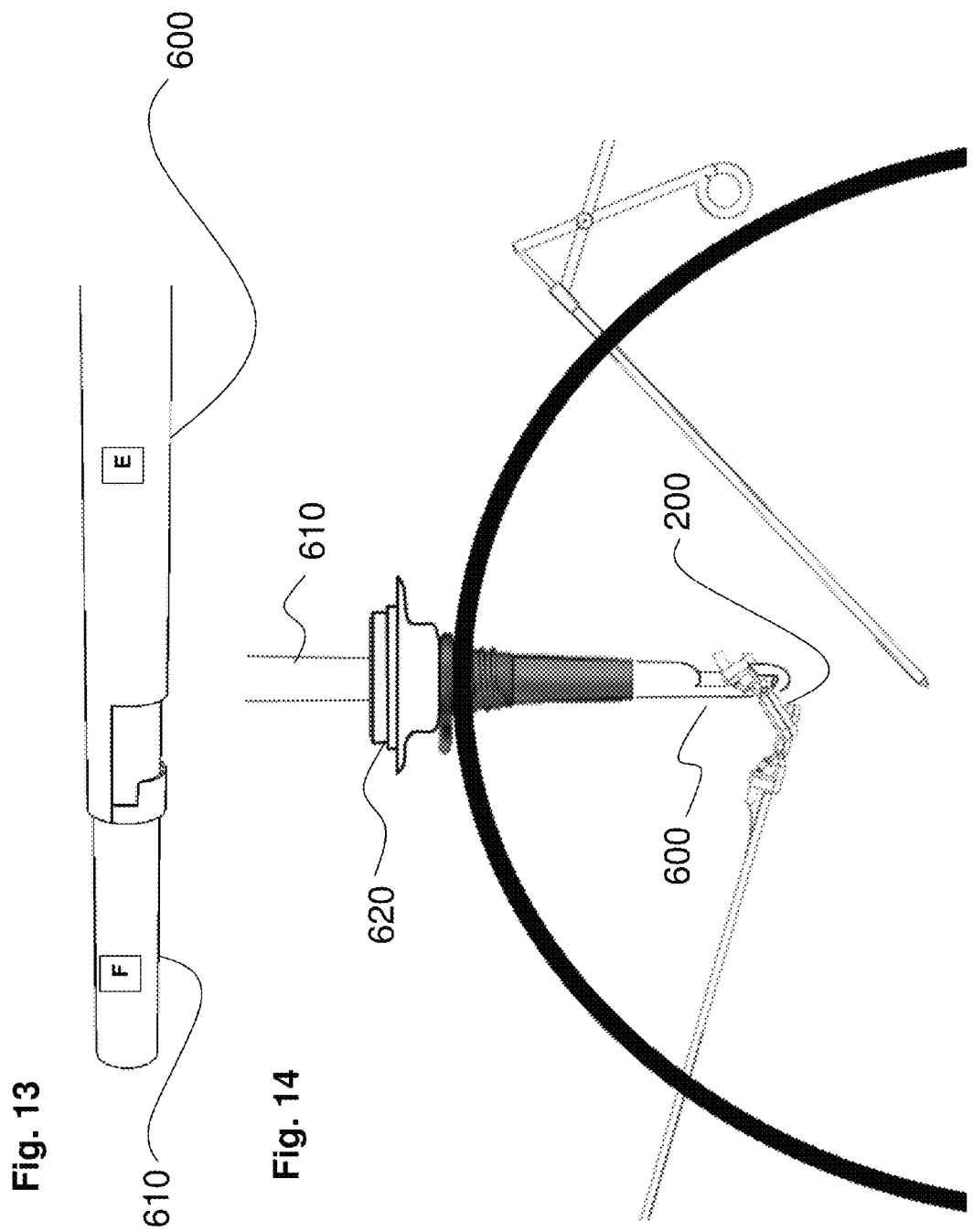

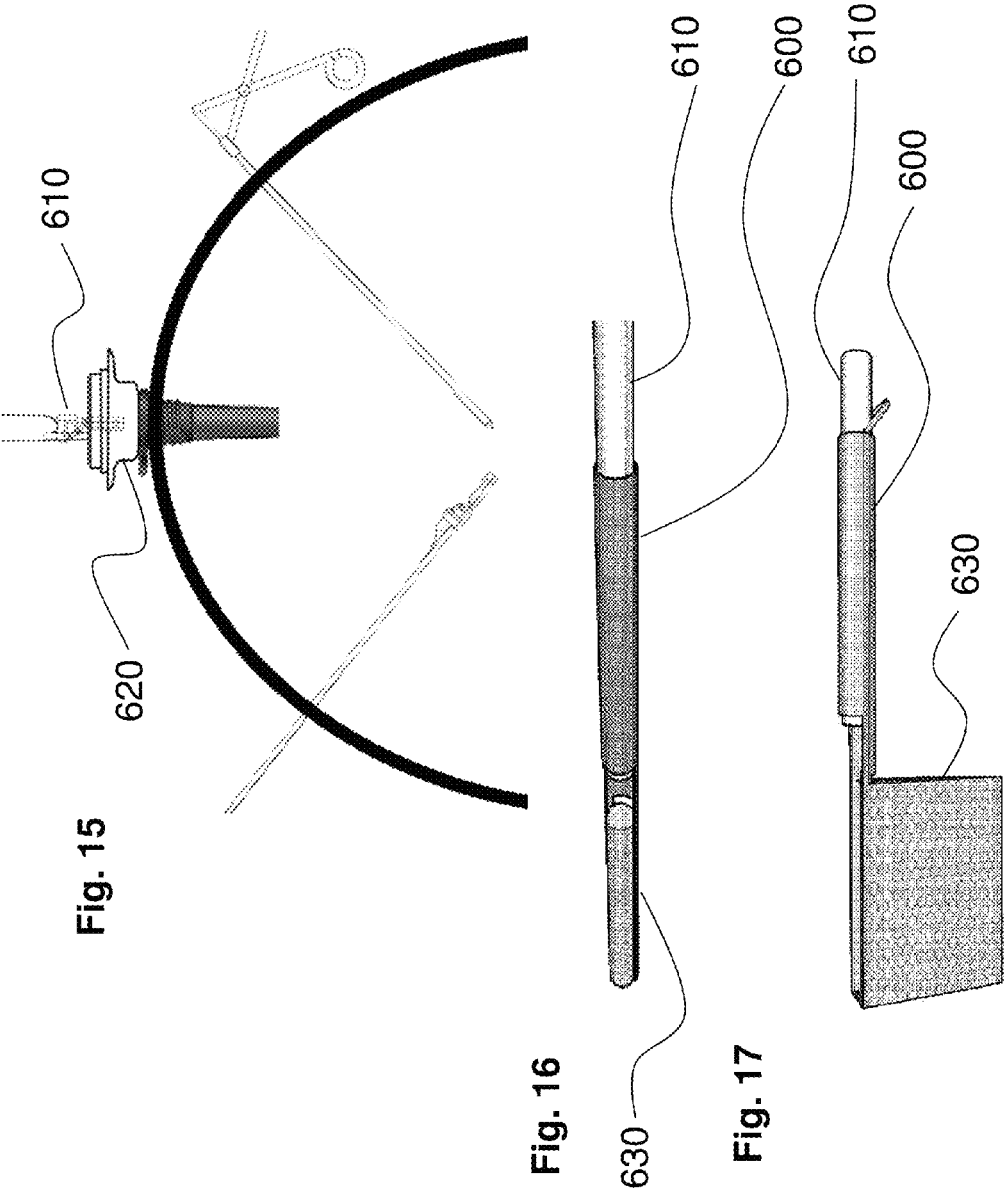

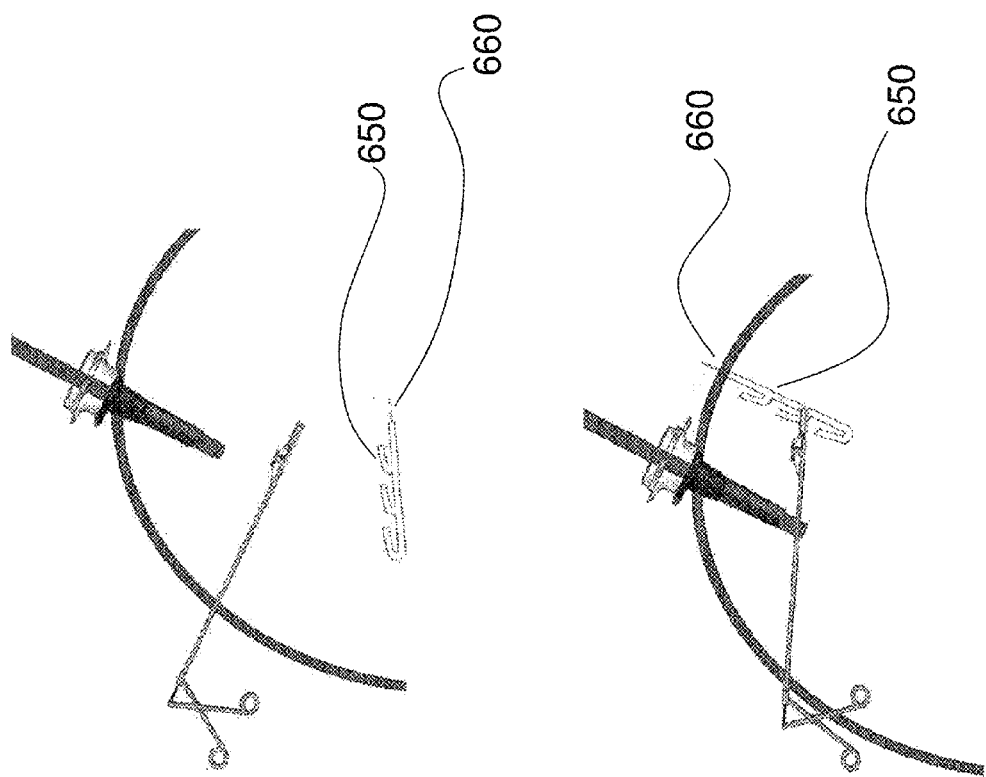

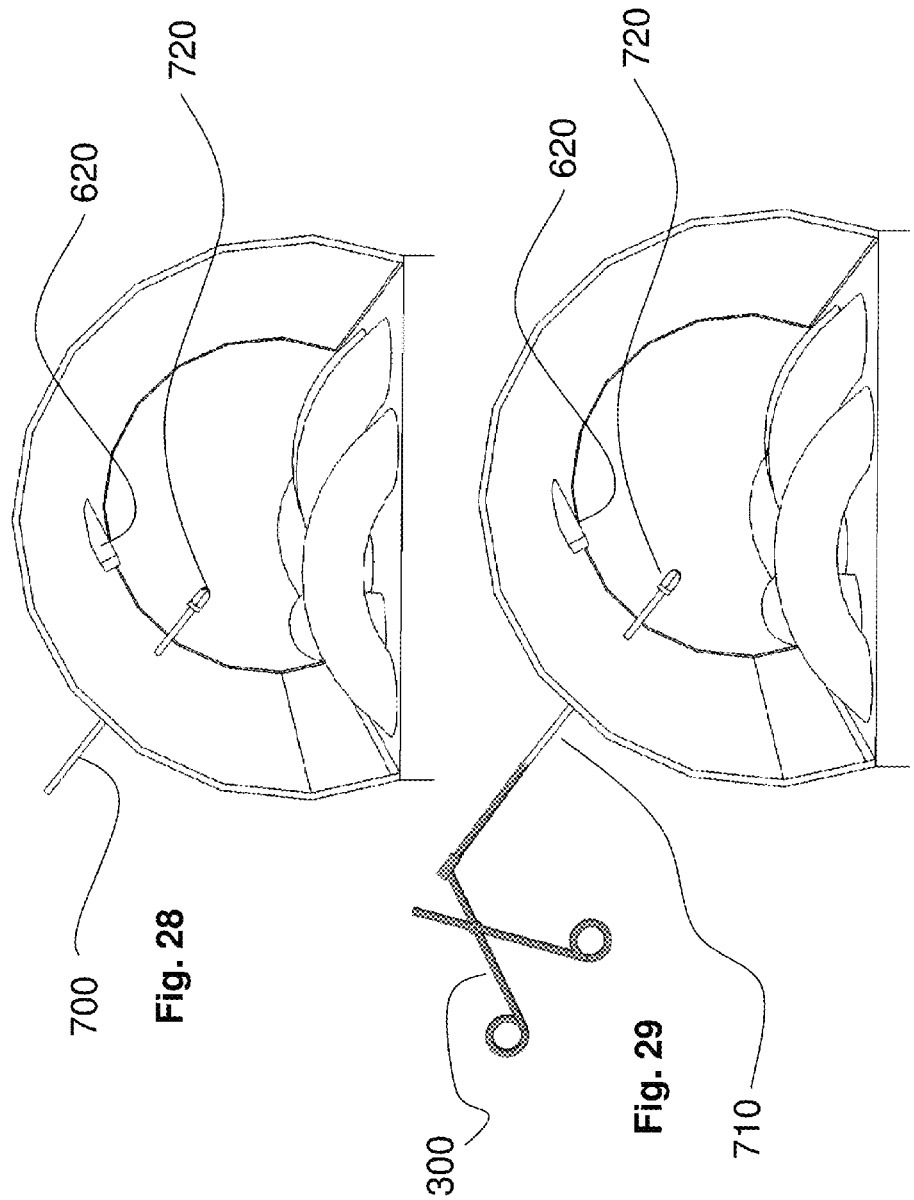

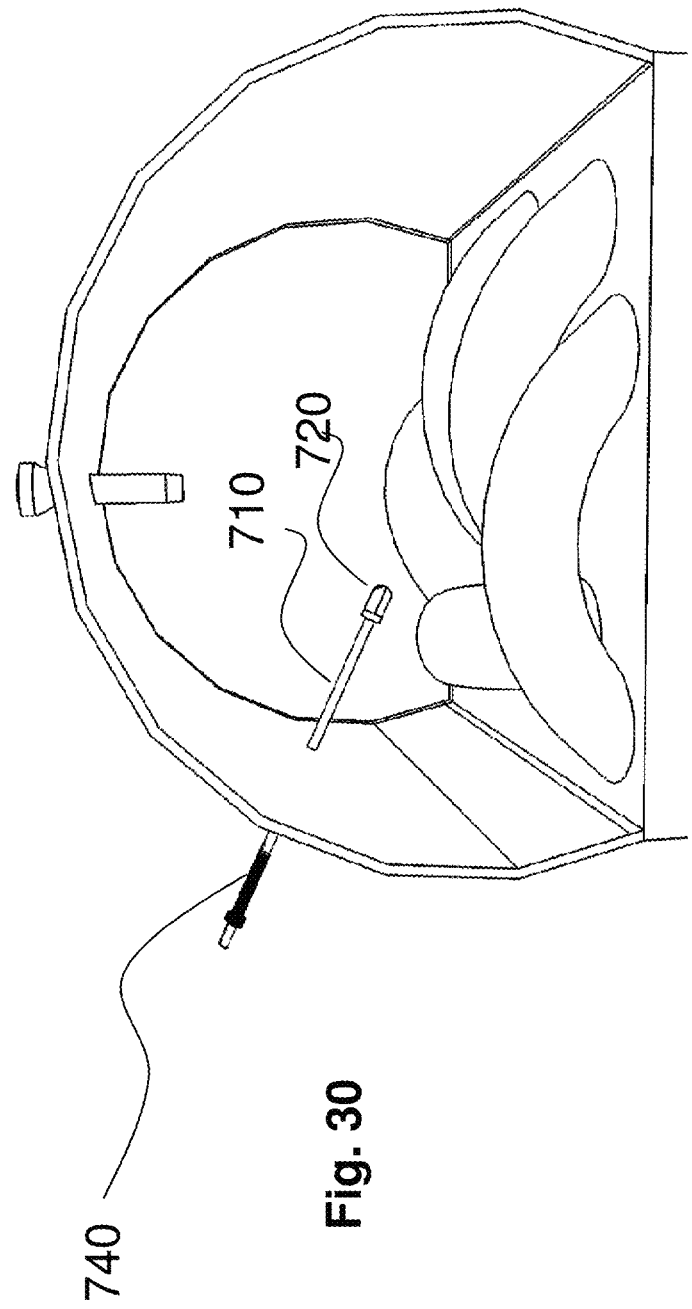

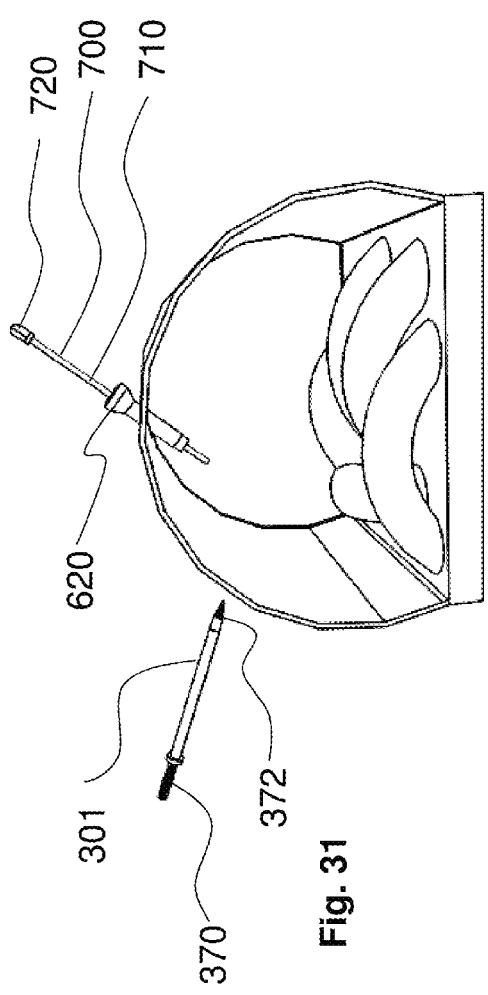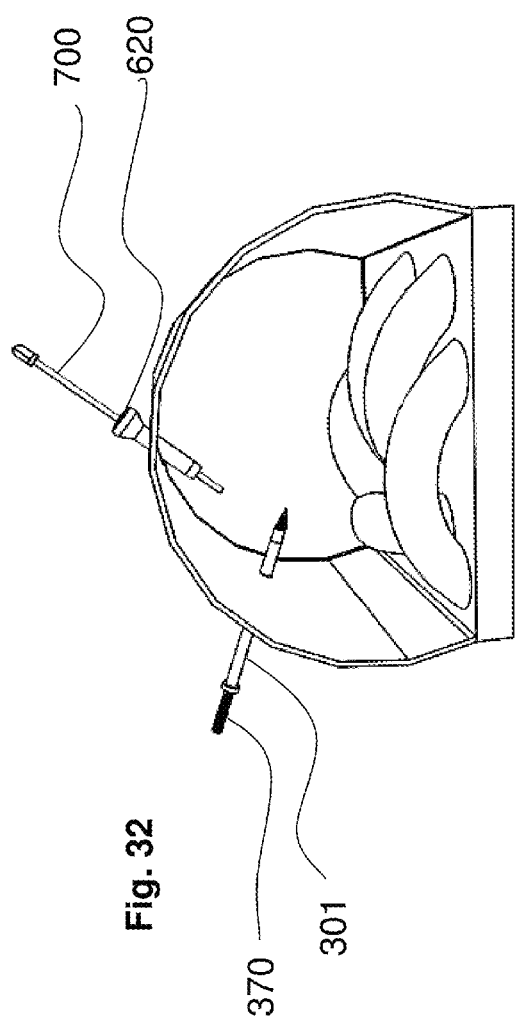

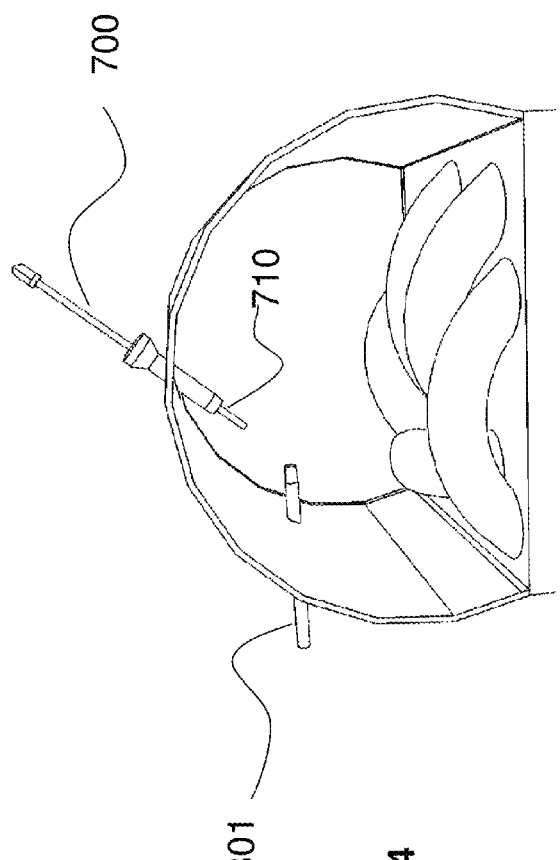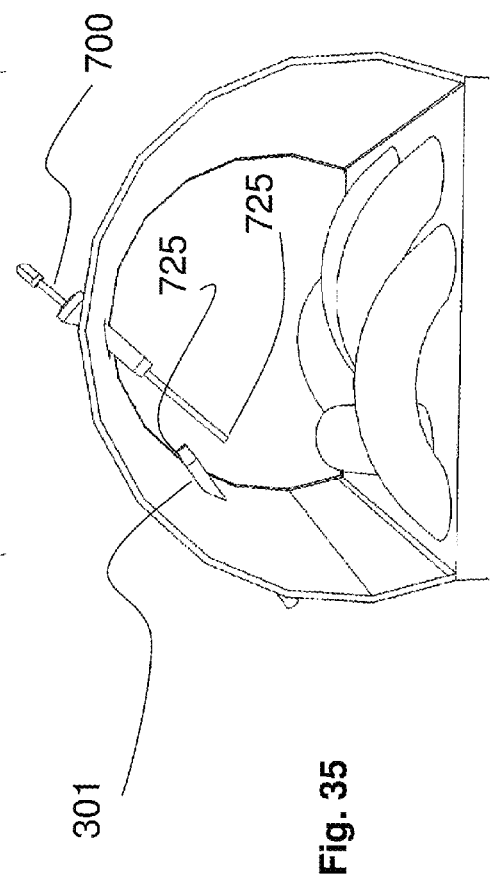

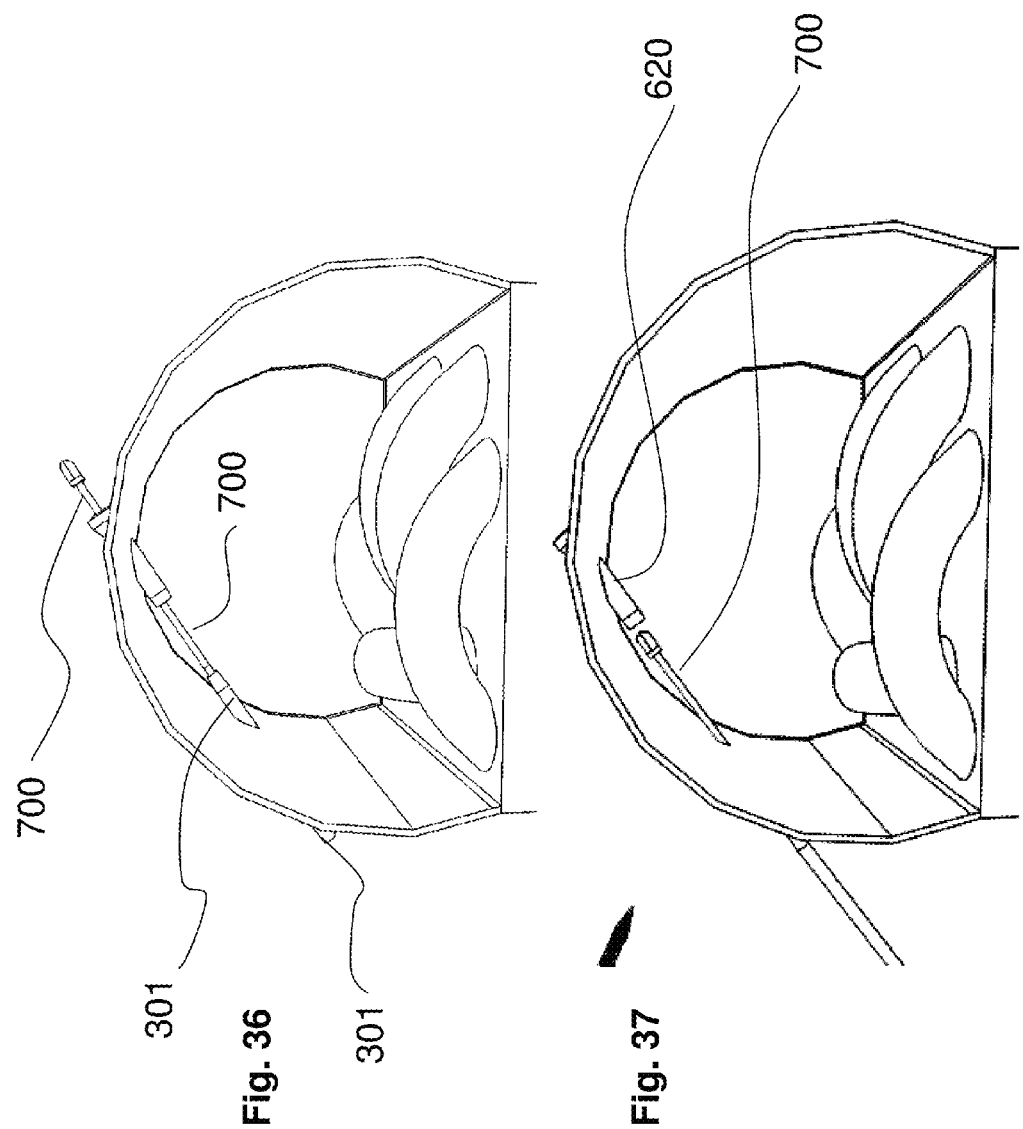

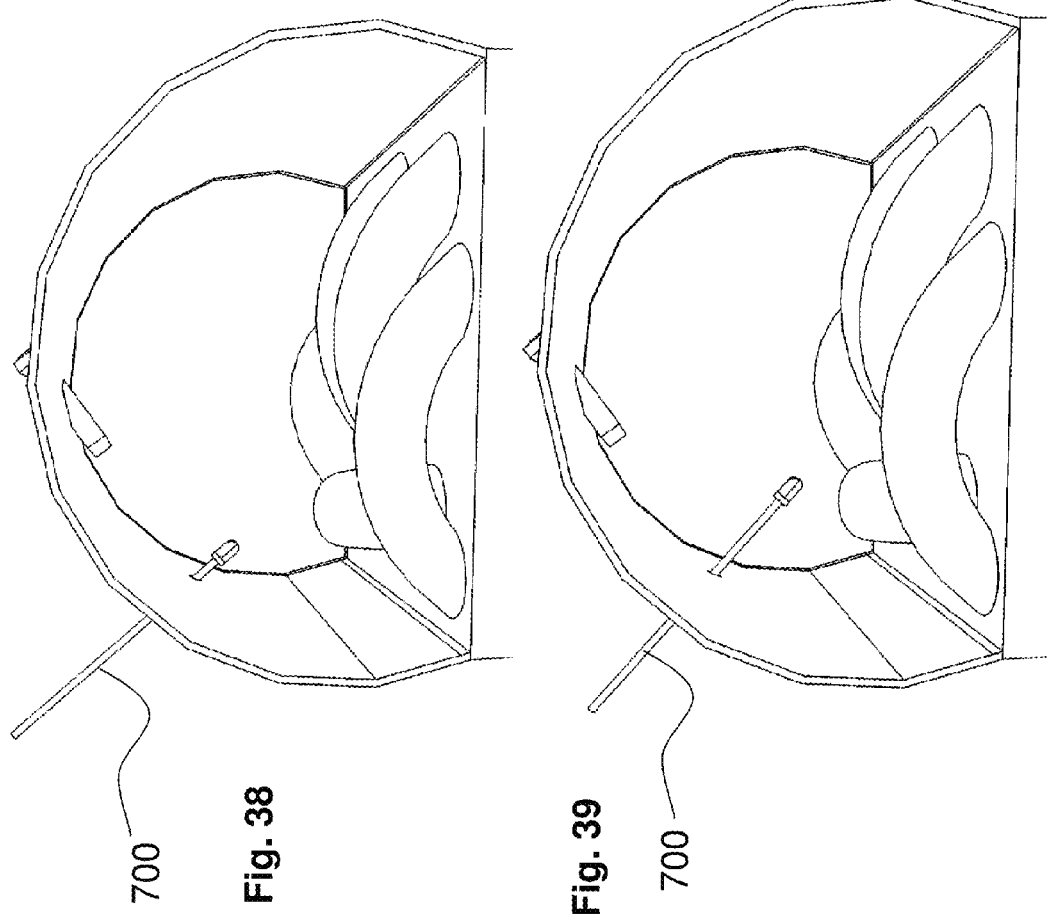

METHODS AND DEVICES FOR LAPAROSCOPIC SURGERY

RELATED APPLICATION/S

This application claims the benefit of priority under 35 USC 119(e) of U.S. Provisional Patent Application No. 61/179,413 filed May 19, 2009, the contents of which are incorporated by reference as if fully set forth herein.

FIELD AND BACKGROUND OF THE INVENTION

The present invention, in some embodiments thereof, relates to devices and methods for performing laparoscopic surgery.

Laparoscopic surgery (one form of minimally invasive surgery (MIS), also known as band-aid surgery, keyhole surgery, or pinhole surgery) is a modern surgical technique with many advantages over traditional open surgical methods. The first use of this approach in order to perform a cholecystectomy was in 1987. Since that time, the procedure has gained popularity and is now regularly used in many different operations within the abdominal and pelvic cavities as well as for thoracoscopic and orthopedic surgery.

In existing laparoscopic methods, a variety of different instruments are used, including graspers, scissors, coagulation devices, harmonic scalpels, needle holders, cameras, suction devices and so on. A plurality of such instruments may be required in a single procedure, with each instrument requiring its own trocar, which both acts as an entry port and facilitates manipulation of the devices within the abdominal cavity or other operative site. In general, laparoscopic operations are usually performed by inserting 2-6 trocars (ports) into the abdominal cavity, each through an incision in the skin.

The trocars usually range in size from 5 mm to 12 mm in diameter, each serving as an introduction channel for one or more surgical tools. However, the use of trocars carries risks during both insertion and removal. The risks include:
- damage to blood vessels in the abdominal walls (particularly in overweight patients);
- damage to fascial tissues;
- extended and painful recovery period;
- visible scarring;
- relatively high cost;
- time consuming; and
- post-operative ventral hernia (POVH), particularly when the larger trocars are used.

Most of the aforementioned risks and disadvantages are associated with the relatively large size of the incision required for trocar insertion.

SUMMARY OF THE INVENTION

The present invention, in some embodiments thereof, relates to devices and methods for performing laparoscopic surgery. More specifically, the present invention provides two-part laparoscopic tools which may be inserted into the body using fewer and/or smaller incisions than those used according to methods of prior art, and other tools for facilitating laparoscopic surgery. Embodiments of the invention significantly reduce surgical risks, simplify surgical procedures, and facilitate rapid patient recovery.

The methods include performing laparoscopic interventions using one or more multi-part instruments, wherein each instrument comprises a shaft (optionally with handle) and one or more operating tools (also called "operating heads" and "operating tool heads") attachable to that shaft. The shafts have a cross-section considerably smaller than most laparoscopic tools of prior art and are designed for direct insertion into the body cavity by puncture penetration or through a relatively small incision, rather than through a conventional laparoscopic port. The handles comprise a screw thread or other attaching mechanism at their distal ends, suitable for attaching an operating head thereto.

In the following the term "wide trocar" refers to a trocar wide enough to enable passage of an operating tool. A typical internal diameter of a wide trocar would be 4 mm or larger, though that size is not to be considered limiting. In the following the term "narrow trocar" refers to a trocar only wide enough to enable passage of a shaft to which an operating tool may be attached. A typical internal diameter of a "narrow trocar" would be 3 mm or less, though that size should not be considered limiting.

Various embodiments presented herein enable providing a plurality of operating tools each connected to an individual shaft and able to be operated independently, using only a single wide trocar, by introducing a plurality of operating tools into the body cavity through the wide trocar, and introducing shafts for those operating tools either through narrow trocars or by using a shaft (optionally with an inserted stiffener) to directly puncturing the cavity wall, thereby creating openings substantially similar in size to the diameter of the shaft. Such openings are considerably smaller than the opening required for a wide trocar, and consequently are less damaging and provide fewer complications, shortened recovery time and less bleeding and less scarring.

Embodiments presented herein include methods for attaching an operating tool to shaft and optionally also to a manipulating handle, including:

a) introducing a distal portion of a shaft into a body cavity, for example by puncturing a wall of the cavity or by introducing the handle through the wall by means of a narrow trocar, introducing an operating tool into the body cavity through a wide trocar, and connecting tool to shaft within the body cavity, b) introducing a distal portion of a shaft into a body cavity, for example by puncturing a wall of the cavity or by introducing the handle through the wall by means of a narrow trocar, extending the distal shaft portion towards and into a wide trocar, advancing the distal shaft portion through the wide trocar so that the distal shaft portion exits the body cavity through the wide trocar, attaching an operating tool to that distal shaft portion while the distal shaft portion is outside the body, and then withdrawing the shaft so that the attached operating tool is retracted into the body cavity where it can be used, and c) attaching an operating tool to a shaft, the shaft optionally having a sharp proximal end, introducing the shaft into a wide trocar, extending it towards an inner portion of a body cavity wall, causing the shaft to traverse to body cavity wall so that the proximal shaft extends outside the body cavity, connecting a handle to the shaft portion which is external to the body cavity, and withdrawing the shaft far enough from the body so that the operating tool is drawn through the wide trocar and into the body cavity, where it can be used.

The operating tools (also called "operating heads" herein) may be any surgical tools, including (but not limited to) graspers, scissors, coagulation devices, harmonic scalpels, LigaSure, needle holders, ligatures, cameras and suction devices. The operating heads may optionally have shaft diameters similar to, or larger than, those of conventional laparoscopic tools. According to some embodiments of methods of use, a plurality of these operating heads may be inserted into the body (e.g. sequentially, through a single trocar port of conventional design, or Gastro-Colonoscopically using a Natural Orifice Transluminal Endoscopic Surgery (NOTES) instrument) and may be mated with and attached to their shafts within the body cavity. In alternative embodiments one or more of such shafts may be inserted into the body cavity, extended out of the body cavity (e.g. sequentially) through a single trocar or a reduced number of trocars, attached to an operating head outside the body, and thence drawn back into the body cavity through the trocar. With either of these methods, the result is a plurality of narrow shafts penetrated into the body cavity through punctures or insertions which are smaller than typical trocar diameters, each shaft mated to an operating head, which may be any conventional surgical tool of normal diameter and capabilities. Additional operating heads may be introduced into the body cavity and operating heads may be switched and exchanged, all within the body cavity, during the course of an operation. A plurality of surgical tools are thereby made available for manipulation and use within a body cavity, though a only a reduced number of trocars (optionally only one) have been used.

Some embodiments of the present invention further comprise
- tools for managing a plurality of operating heads within the body cavity, comprising a plurality of connecting elements each able to hold an operating head, and further comprising a penetrating element operable to penetrate a body wall from within the body cavity, and to extend beyond the body where it may be grasped and immobilized from outside the body;
- tools for inserting operating heads into the body cavity and/or for removing operating heads from a body cavity, optionally implemented as a sheath adaptable over a camera assembly introduced into a body through a trocar;
- tools for removing body tissues or other objects from the body cavity during an intervention, comprising a sheath (optionally adaptable over a camera assembly introduced into the body through a trocar) and a rolled or folded bag which may be introduced into the body cavity through the sheath, unrolled or unfolded within the body cavity, filled with materials to be extracted, and then withdrawn from the body through the trocar;
- tools for stabilizing and/or immobilizing and/or positioning body organs or other tissues during a surgical intervention comprising a narrow shaft having a distal portion insertable into the body cavity and connectable to an operating head, and a stabilizing/positioning mechanism connected proximal portion of the shaft outside the body and designed to stabilize the shaft in a selected position; and
- several grasper designs with detachable heads, some including a head mechanism presenting advantages over head mechanisms known to prior art.

It is noted embodiments of the present invention include (and are not limited to) the above-listed components and embodiments used both separately and/or in concert, and further include additional components and embodiments as detailed below. It is further noted that the "wide" and "narrow" tools described in detail below may be used individually or in sets of several such tools used individually and/or in concert, and that one or more "wide" tools may be used alone or in concert with one or more "narrow" tools. It is further noted that the invention is not limited to the specific exemplary uses described for the disclosed devices, and that the invention is also not limited to the specifically described exemplary tool examples described as being used to perform the disclosed methods.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2, 3, 4 and 5 are simplified schematics showing components of the tool shown in FIGS. 1A and 1B;

FIGS. 6C, 6D and 6E show uses for the hollow grasper head shown in FIGS. 6A and 6B, according to embodiments of the present invention;

FIG. 7 is a schematic of a laparoscopic tool with electrical functions, according to an embodiment of the present invention;

FIG. 8 is a narrow laparoscopic tool according to an embodiment of the present invention;

FIG. 9 is a grasper head showing opening and closing of the grasper, according to an embodiment of the present invention;

FIGS. 11A, 11B, 11C and 11D show details of connection between a shaft and a handle, according to an embodiment of the present invention;

FIG. 13 presents a tool for manipulating operating heads within a body cavity;

FIGS. 14 and 15 present examples of the use of the tool shown in FIG. 13, according to an embodiment of the present invention;

FIGS. 16, 17 and 18 present several embodiments of a tool for removing materials from a body cavity, according to an embodiment of the present invention;

FIGS. 20, 21 and 22 present stages in the use of the tool shown in FIG. 19, according to an embodiment of the present invention;

FIGS. 24, 25, 26, 27, 28 and 29 present stages in a process for introducing and using a surgical tool with a wide head in a body cavity using only a small incision, according to an embodiment of the present invention;

FIG. 30 presents an optional enhancement to the method shown in FIGS. 24-29, according to an embodiment of the present invention; and FIGS. 31, 32, 33, 34, 35, 36, 37, 38 and 39 present aspects of a surgical procedure whereby a tool with wide operating head and narrow shaft may be introduced into a body cavity, according to an embodiment of the present invention.

DESCRIPTION OF SPECIFIC EMBODIMENTS OF THE INVENTION

Figure 1A:
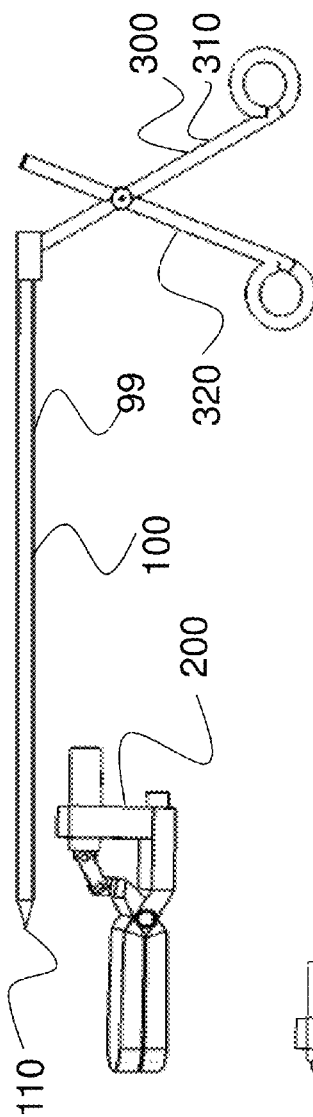
FIGS. 1A and 1B are simplified schematics of a two-part laparoscopic tool, according to an embodiment of the present invention.

The present invention, in some embodiments thereof, relates to devices and methods for performing laparoscopic surgery. More specifically, the present invention provides two-part laparoscopic tools which may be inserted into the body using fewer and/or smaller incisions than those used according to methods of prior art, and other tools for facilitating laparoscopic surgery. Embodiments of the invention significantly reduce surgical risks, simplify surgical procedures, and facilitate rapid patient recovery.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

It is expected that during the life of a patent maturing from this application many relevant laparoscopic tools will be developed and the scope of the terms "laparoscopic tool", "operating tool" and "operating head" are intended to include all such new technologies a priori.

The terms "comprises", "comprising", "includes", "including", "having" and their conjugates mean "including but not limited to".

The term "consisting of means "including and limited to".

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

According to some embodiments of the invention there is presented a method for inserting and removing surgical instruments during a laparoscopic procedure in the body cavity of a subject, comprising inserting a surgical instrument (a grasper, for example) constructed of two separate parts, a distal operating head inserted into a body cavity through a conventional laparoscopic port, by use of a Natural Orifice Transluminal Endoscopic Surgery (NOTES) instrument, or by some similar method, and a proximal shaft directly inserted into a body cavity through a stab incision made in the wall of the body cavity;

connecting the two parts of the instrument;

use of the instrument within the body cavity separation of the two parts following their use;

withdrawal of the shaft through its stab incision; and withdrawing of the distal operating head through the port, NOTES instrument, or similar device.

Connecting and separating distal and proximal portions of the device may be performed with the assistance of a conventional grasper inserted through a trocar.

In some embodiments of the invention a surgical kit comprises a "wide tool" and one or more "narrow tools".

Figure 1B:
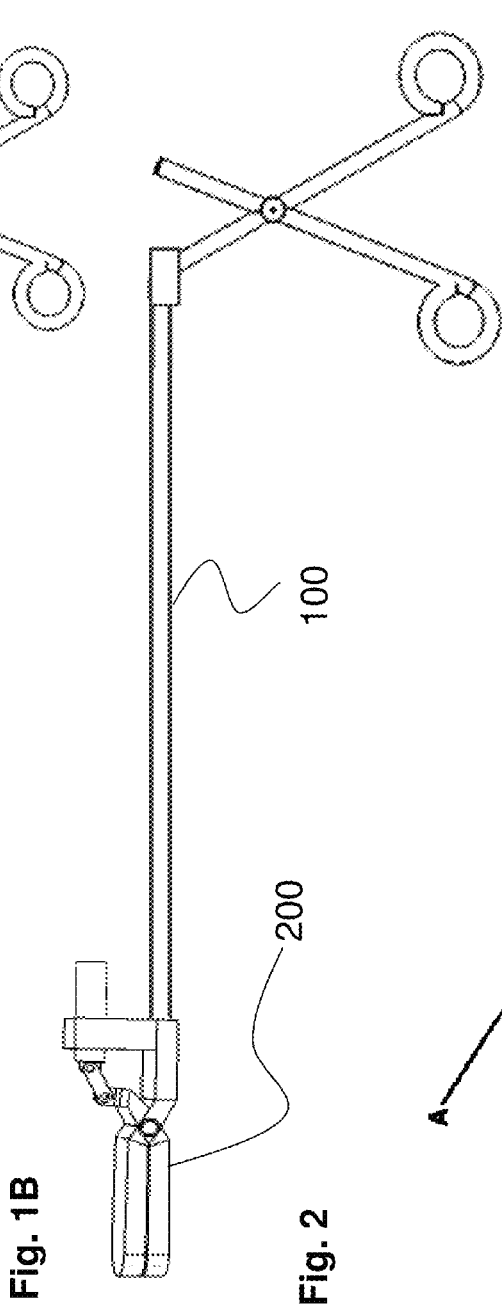

FIG. 1A presents an exemplary embodiment of a wide tool 99, comprising a shaft 100 with a sharp distal end 110 capable of penetrating a body wall, and a detachable head 200. FIG. 1B shows a wide tool with detachable head 200 attached.

In some embodiments the shaft of the wide tool is inserted into a body cavity through the cavity wall, and the distal head of the wide tool is inserted into the body cavity through a trocar and connected to the wide tool shaft by manipulation by a grasper or other tool inserted through a trocar. In other embodiments the distal portion of the wide tool may be caused to traverse a portion of the body cavity, and exit the cavity through a trocar, where the wide tool head can be connected to the wide tool shaft, which is then retracted into the body cavity. In yet other embodiments the wide tool with head attached may be inserted into the body cavity through a trocar.

Once the wide tool head is connected to the wide tool shaft and positioned in the body cavity, the wide tool can be used as described below to connect additional operating heads to additional tools having shafts introduced (by puncture or very small incisions) into the body cavity. These may be additional wide tools and/or "narrow tools" as described below.

As may be seen in the exemplary embodiment shown in FIG. 1, the shaft of the wide tool may be implemented with a proximal handle 300 shaped similarly to a scissor, with one leg of the scissor attached to the outside of the shaft, and a second leg attached on an actuating rod or actuating cord passing the length of the shaft and providing means for manipulating an operating head when attached thereto by pulling or pushing on the actuating rod or cord and causing it to move backward or forward with respect to the body of the shaft.

Figure 2:
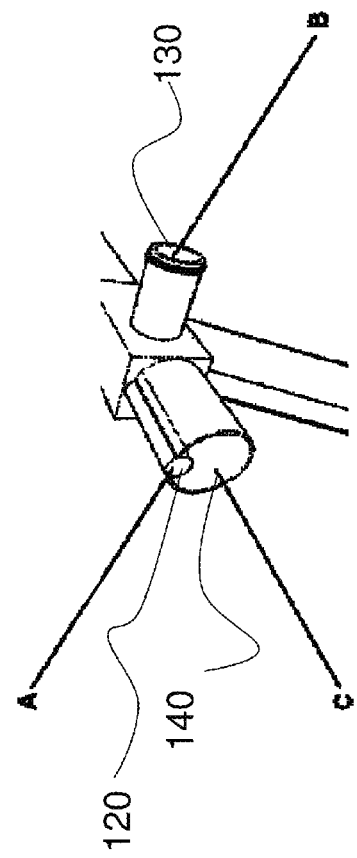

FIG. 2 shows a portion of a distal part of such a shaft, showing at "A" a passageway 120 for such an actuating cord 125 or rod 127, at "B" a connector 130 for fluid (e.g. irrigation or suction), and at "C" a passageway 140 for a stiffening rod 150. FIG. 3 shows such a stiffening rod 150 positioned alongside the shaft 100 of a wide tool 99, and FIG. 4 shows the stiffening rod 150 inserted therein. Such a stiffening rod can be inserted in the shaft 100 to stiffen and reinforce the shaft, for example when the shaft is caused to penetrate by force through a body wall or other tissue. The stiffening rod can then be removed, leaving an empty passageway 140 through which fluids can be caused to flow (e.g. for suction or irrigation), or which may be used for other purposes such as passing objects therethrough.

Figure 5:
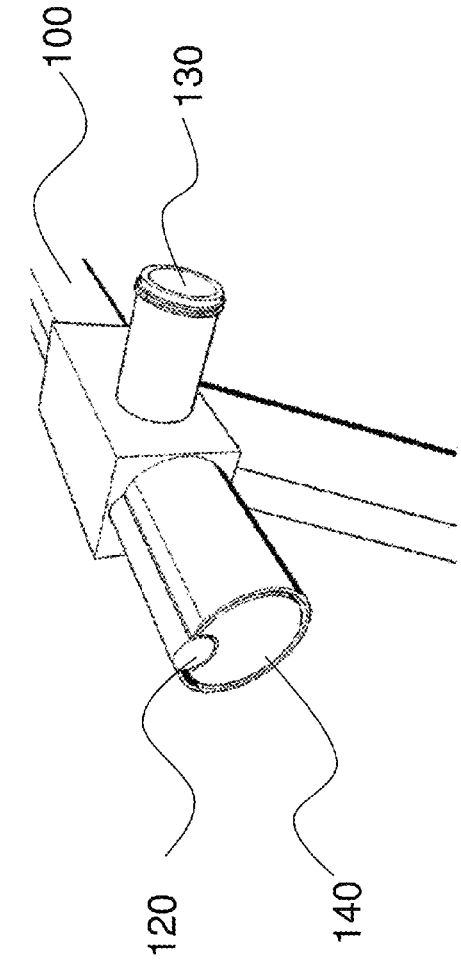

FIG. 5 presents an additional embodiment where similar elements are presented in a slightly different configuration. It is noted that the small passage 120, described above as used for passage of an actuating rod 127 or cord 125, can be used for other purposes, such as for passage of an electrical connection 129. Additional conduits within the shaft may be supplied as well.

Figure 6A:
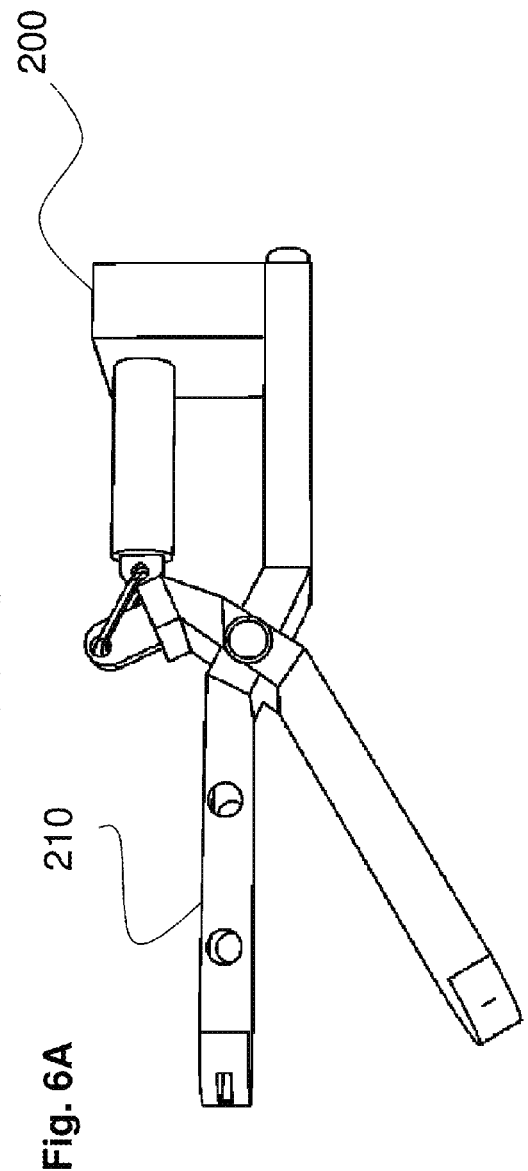
FIGS. 6A and 6B are simplified schematics showing a hollow grasper head.
Figure 6B:
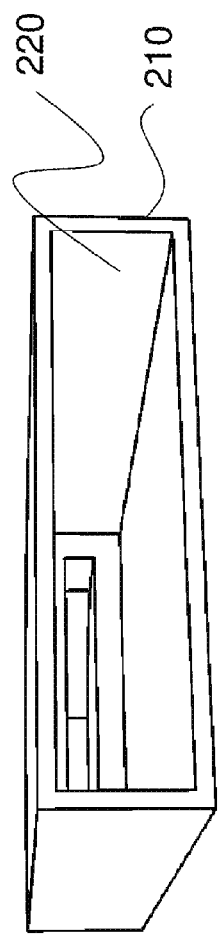

The wide tool may be provided with a solid grasper head, or with a grasper head 210 comprising hollow portions 220 which can be used as conduits for fluids. Such a head 210, comprising a hollow 220, is shown in FIG. 6A, and a detail view of the hollow portion of such a head is shown in FIG. 6B. This hollow portion 220 can be made continuous with the passage 140 shown in FIG. 2, or with another conduit in the shaft, to enable irrigation, suction, or some similar fluid-related activity. It is noted that although a grasper head with a hollow portion is shown in the figures in the context of tools with detachable heads as described above, graspers and similar surgical tools which comprise hollow portions and are capable of implementing suction activity or irrigation activity in addition to grasping may also be implemented in surgical instruments wherein the grasper head is permanently attached to its shaft.

Figure 6C:
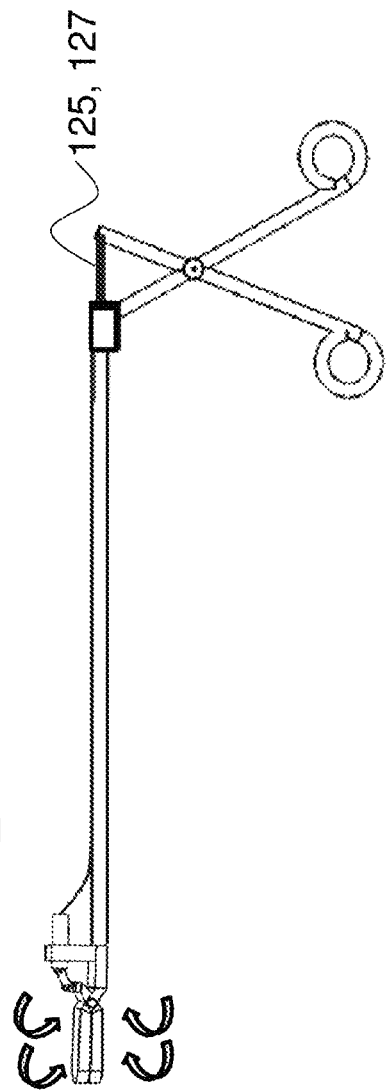
Figure 6D:
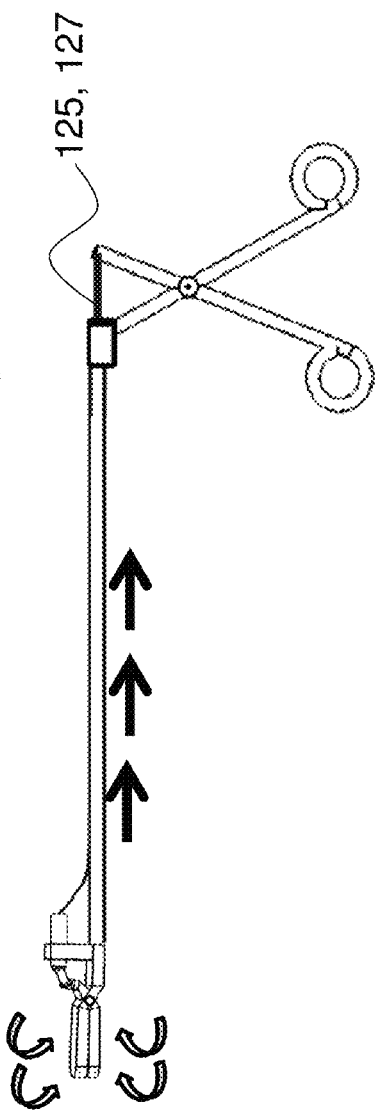

FIGS. 6C, 6D, and 6E show successive stages of fluid flow in the case of suction being applied at point "B" of FIG. 2.

Optionally the wide tool may comprise an electrical power connection, and portions of the shaft may be constructed of insulating materials or may be covered by insulating materials, as appropriate. Electrical tools 270 may be positioned at the operating head or may be incorporated in the shaft. An example is provided in FIG. 7, which presents a wide tool configured as a coagulator 272.

FIG. 8 presents a partial view of a "narrow tool" 101, one or more of which are supplied together with at least one "wide tool" to form a kit, in some embodiments of the present invention. A narrow tool is similar to a wide tool in that it comprises a shaft which comprises a distal end sharp enough to penetrate tissue, a separable operating head useful for performing a useful function during a surgical procedure, and an attachment configuration (for example, screw threads) enabling to attach and the operating head to a distal portion of the shaft, and to detach it therefrom. In some embodiments the narrow tube comprises a conduit through which a wire and/or an activating rod or cord may be passed, which wire or rod or cord may be used to control or activate the operating head or a portion thereof. Such a conduit is seen positioned in an upper portion of that part of a narrow tool shaft pictured in FIG. 8.

It is an advantage of the narrow tool that it may be made extremely thin: in some embodiments the diameter of a narrow tool is between 1 and 3 mm. (Note that these dimensions are given by way of example, and are not to be considered limiting.) Thin shafts of such narrow dimensions can be caused to penetrate through an abdominal wall (or into any other body cavity) with a minimum of damage to tissues through which they pass. In an exemplary method of use, a wide tool is introduced into a body cavity as described above, an operating head for a narrow tool is introduced into a body cavity through a trocar, and the wide tool is used to grasp the detached narrow-tool head and to attach it to the narrow tool shaft. In this manner one or many narrow tools can be introduced into the body cavity and used within the cavity with only minimal damage to the cavity walls. Narrow tools so introduced are similar to standard laparoscopic tools and can be used by a surgeon with little or no special training.

In some embodiments the operating head is constructed of two parts, a base part connected to the shaft (e.g. to a wide tool shaft or to a narrow tool shaft), and a second moveable part connected to an activating rod positioned in a conduit within the shaft. Moving the activating rod forward and backward has the effect of moving the moveable head part with respect to the base head part, for example opening and closing a grasper as shown in FIG. 9.

Figure 10:
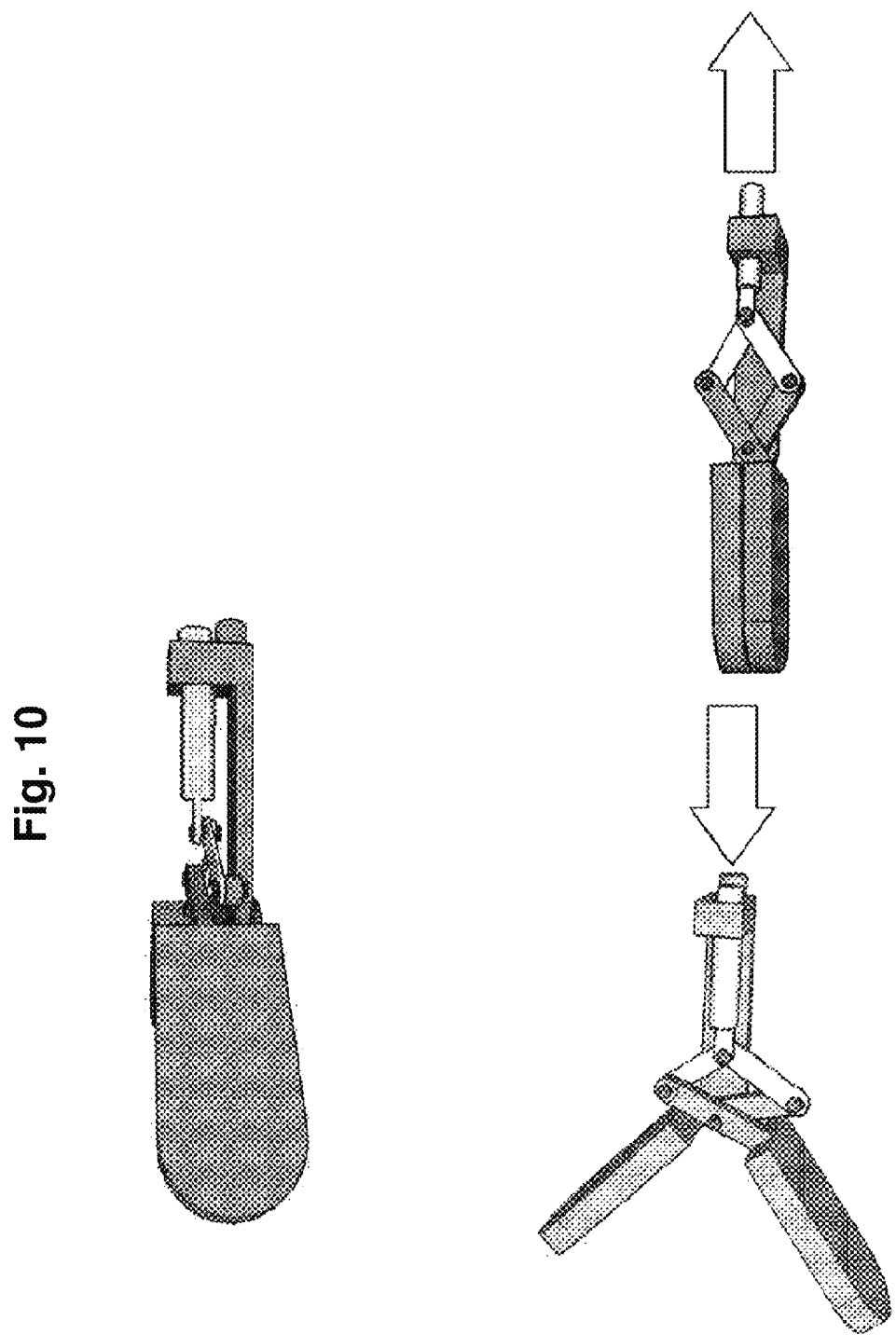
FIG. 10 shows several views of an additional construction of a grasper head according to an embodiment of the present invention.

In an alternative construction shown in FIG. 10, two moveable parts each connected to a common activating rod are also connected to a fixed part of a shaft. Forward and backward movement of the activating rod with respect to the shaft has the effect of closing and opening the moveable portions of the grasper, as shown in the Figure.

A further alternative construction is presented in FIG. 11, which shows a configuration in which an external activating rod connects to an external portion of an operating head, and an internal activating rod, able to advance and retract within the external portion, connects to an internal portion of the operating head. Advancing and retracting the internal rod with respect to the external portion causes opening and closing of the jaws of the grasper. Also of interest in the Figure: note the form of the distal portion of the shaft 100 in FIGS. 11A and 11D, which distal portion is pointed (102) to facilitate penetration of tissues, but which also comprises screw threads 104 enabling connection between shaft and head. Note also the matching screw threads 103 on outer and inner portions of the operating head, as shown in FIGS. 11B and 11D.

Figure 12:
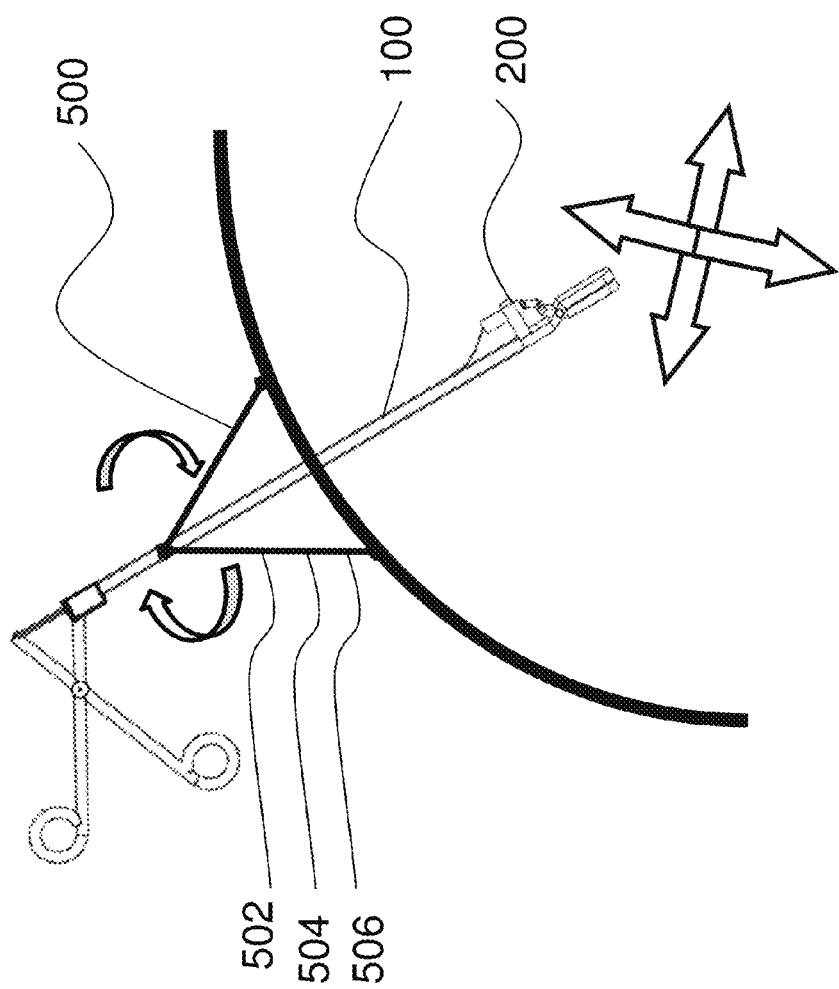
FIG. 12 presents a immobilization device for surgery according to an embodiment of the present invention.

Surgical Support Tools:

Physical Support Structure:

In some embodiments of the invention there is provided a support structure 500 which enables to physically support or hold organs or parts of organs or other tissues in particular positions, to enable surgical work to proceed on those organs or tissues, or on organs or tissues in their vicinity. FIG. 12 provides a view of an embodiment where a wide or more typically a narrow tool is used for this purpose. The distal portion of the tube is made to penetrate into the body cavity, the operating head 200 is attached as described above, and the operating head 200 (in the form of a grasper or other tool) is made to seize and hold a portion of the organ or tissues whose support or immobilization is desired. As shown in the figure, an external support device 500 surrounding or otherwise connected to a proximal portion of the tool shaft 100, outside the body cavity, is adjustable and may be adjusted to maintain that proximal portion at a desired position and angle with respect to the body. (In the exemplary embodiment shown in the figure, a tripod 502 or multi-legged shape 504 with adjustable-length legs 506 is used.) Fixing the position of the proximal portion, external to the body, also fixes the position of the distal portion internal to the body, and thereby fixes also the position of the tissue or organ grasped by the head.

Tool for Removal of Operating Heads:

FIGS. 13-15 present a tool for removal of operating heads from within the body cavity. FIG. 13 shows the head removal tool in the form of a sleeve 600 formed to fit on a camera or other visualization device 610 introducible into a body cavity through a trocar 620. At the end of the operation or whenever desired, the visualization device may be withdrawn from a trocar, a sleeve "E" added to the device as shown in FIG. 13, and the device reinserted. In use sleeve E may be extended beyond the visualization device. A wide or narrow tool is used to detach an operating head 200 from a tool, and to position it within or attach it to sleeve 600 as shown in FIG. 14. The visualization device 610 together with sleeve 600 and the attached operating head 200 can then be removed through the trocar as shown in FIG. 15.

Figure 18:
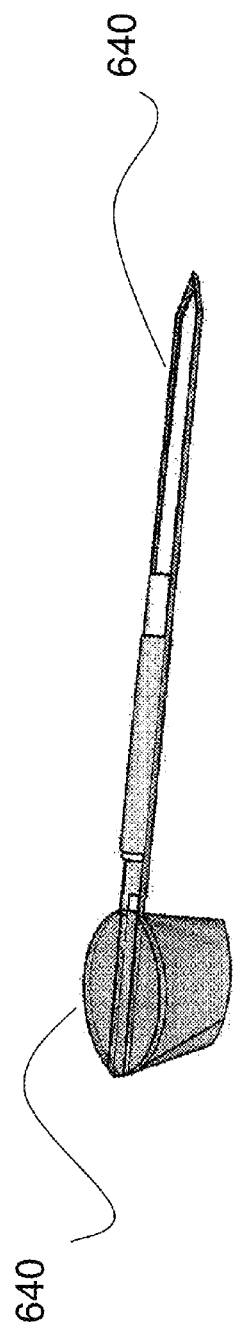

Device for Extracting Tissues:

During the course of an operation it is often necessary to provide for removing from a body cavity organs or tissues which have been excised, or to provide from removing devices introduced into the cavity during the operation. FIGS. 16-18 present a device for doing this.

As shown in FIG. 16, a sleeve 600 is provided which is sized and shaped to be adapted to a visualization device 610 insertable into the body through a trocar 620 or other port. An appropriately sized bag 630 is rolled or folded and stored within the sleeve.

When deployment of the bag is desired, the bag 630 may be unrolled or unfolded using a manipulation device (such as narrow or wide tool with grasper head) present in the body cavity. The deployed removal bag 630 is shown in FIG. 17.

In an alternative embodiment, the removal bag may be provided with flexible straps 640 as shown in FIG. 18. The straps may be manipulated to open the bag for use, and the bag may be removed from the body cavity by pulling on the straps, which extend beyond the trocar and may be grasped from outside the body of the patient.

Tool for Managing Operating Heads:

According to a further aspect of embodiments of the invention, there is provided a tool for managing a plurality of operating heads within the body of a patient.

As described above, operating heads may be inserted into a body cavity (e.g. through a trocar) and there may be attached to one or more tool shafts. In some cases it may be desired to have a plurality of operating heads (e.g. a plurality of tools of different types) present within a body cavity, and to alternate use of various heads by attaching and disconnecting them from one or more tool shafts, which shafts remain in place and need not be removed from the cavity nor reinserted therein.

Figure 19:
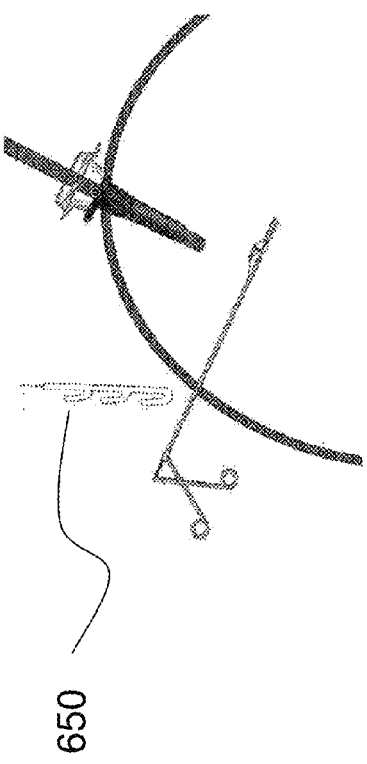
FIG. 19 presents a tool for organizing treatment heads within a body cavity.

To facilitate this process a tool organizing device is provided, as shown in FIGS. 19-21.

The tool organizing device may be configured as a cartridge magazine, as a rack, as a shelf, as a set of hooks, or in any other convenient configuration.

FIG. 19 shows an exemplary tool rack 650 (a tool organizer device 650 or "head storage tool" is configured as a set of connected hooks) is shown external to the body cavity.

In FIG. 20, the tool organizer device (head storage tool) has been inserted into the body cavity, e.g. through a trocar. To avoid multiplying large body openings, if a single trocar has been installed and is used for passage of a visualization device into a body cavity, passing the tool organizer (or tool operating heads, or other objects) into the cavity may be done, for example, by removing a visualization device from a trocar, passing the organizing device through the trocar into the cavity, and then replacing the visualization device in the trocar.

As shown in the Figure, the tool organizer comprises a penetrating point 660 long enough and sharp enough so that if the device is grasped by a tool within the cavity the penetrating point may be caused to pass from inside the cavity to the outside of the body, where it may be grasped and held by a surgical tool. This has the effect of immobilizing the tool organizer as shown in FIG. 21.

Figure 22:
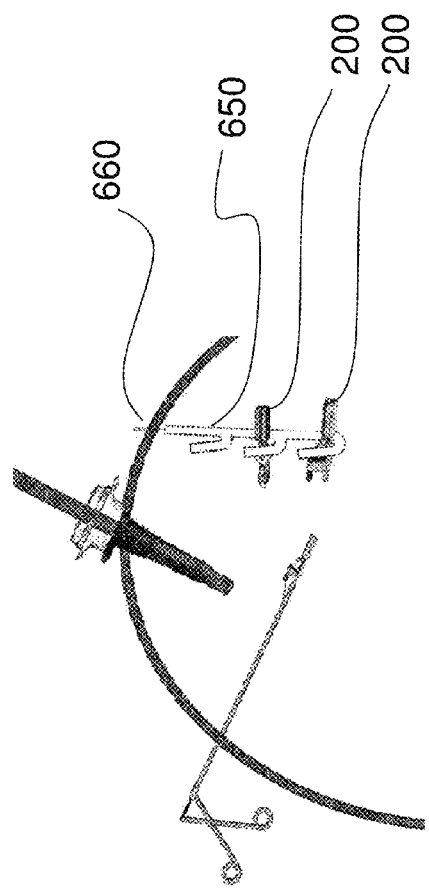

A plurality of operating heads may then be stored in or on the device during an operation, where they are accessible to being taken up by one of the available manipulating tools (e.g. wide tool or narrow tool), yet are kept in order and out of the way of on-going surgical manipulations. This situation is presented in FIG. 22.

Figure 23:
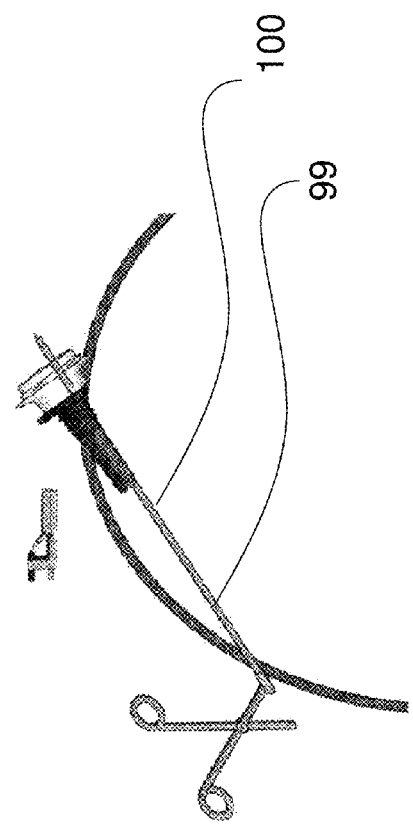
FIG. 23 presents a method for attaching a treatment head to a shaft according to an embodiment of the present invention.

Attention is now drawn to FIG. 23 which shows a process whereby an operating head 200 may be attached to a penetrating tool 100 while outside the body, as was mentioned above. This procedure is convenient for attaching an operating head to a wide tool, which wide tool can then be used to attach operating heads to a plurality of narrow tools within the body cavity. However, for convenience, the procedure shown in FIG. 23 can be used to attach heads to narrow tools as well.

As seen in the figure, a shaft 100 is caused to penetrate into a body cavity in which a trocar 620 or similar port has been inserted. The shaft is then directed towards and through the trocar (a visualization device using the trocar may be temporarily removed from it for this purpose), and becomes available outside the body, where the operating head may be attached. The shaft is then withdrawn through the trocar back into the body cavity, where it may be used. A similar procedure can be utilized to remove a head from a shaft before withdrawing the shaft from the body.

Example of a Surgical Procedure Using Tools Described in this Document: Removal of an Appendix.

- Insert standard trocar (e.g. trocar of 10 mm diameter) into a body cavity wall, e.g. in the navel;
- Insert a visualization modality (e.g. a camera), use it to survey the body cavity, locate the infected appendix
- Insert wide tool directly into lower belly
- Temporarily remove visualization device, pass through the distal portion of wide tool so that it extends beyond the trocar and is outside the body.
- Affix operating head to wide tool.
- Withdraw wide tool through trocar into body cavity, replace visualization device.
- Introduce narrow tool into the lower belly above the pubis under guidance of visualization device.
- Remove visualization device from trocar, introduce operating head (e.g. dissector) through trocar, restore visualization device.
- Use wide tool to grasp dissector head and affix it to narrow tool shaft, under guidance of visualization tool
- Remove visualization device from trocar, introduce tool organizer, scissor tool, and a tool for immobilization of the intestine.
- Fix tool organizer in a place by holding with wide tool and causing its penetrating point to penetrate the body wall to a position outside the body, where it is grabbed by a standard surgical device, thereby immobilizing it.
- Mount spare operating heads on the organizing tool.
- Proceed with the operation, cutting, cauterizing, etc. according to standard surgical procedures as needed, using the various tools held in readiness by the tool organizer, and changing operating heads as needed. Appendix is disconnected from the body, bleeding is cauterized and/or tied. Scissor head mounted on one of the shafts and used to cut ligatures.
- Visualization tool removed, sleeve containing tissue bag is mounted on visualization device which is returned to place through the trocar.
- Bag is opened using narrow tool, appendix placed within bag, bag and visualization device removed from body through trocar. Visualization tool replaced in cavity.
- Operation site is irrigated through hollow portion of wide tool. Hemostasis checked.
- Body cavity is irrigated, cleaned, inspected
- Head removal tool mounted on visualization tool and used to remove various operating tools, and (usually last) the tool organizer
- Narrow tool(s) withdrawn from body under observation by visualization tool. Generally no stitching of the penetration site is required.
- Removal of visualization device, then of the trocar. Closing of the opening through which the trocar was inserted.

Attention is now drawn to FIGS. 24-29 which show additional methods for providing a plurality of operating tools with wide heads within a body cavity having only a single wide opening.

Figures 24, 25:
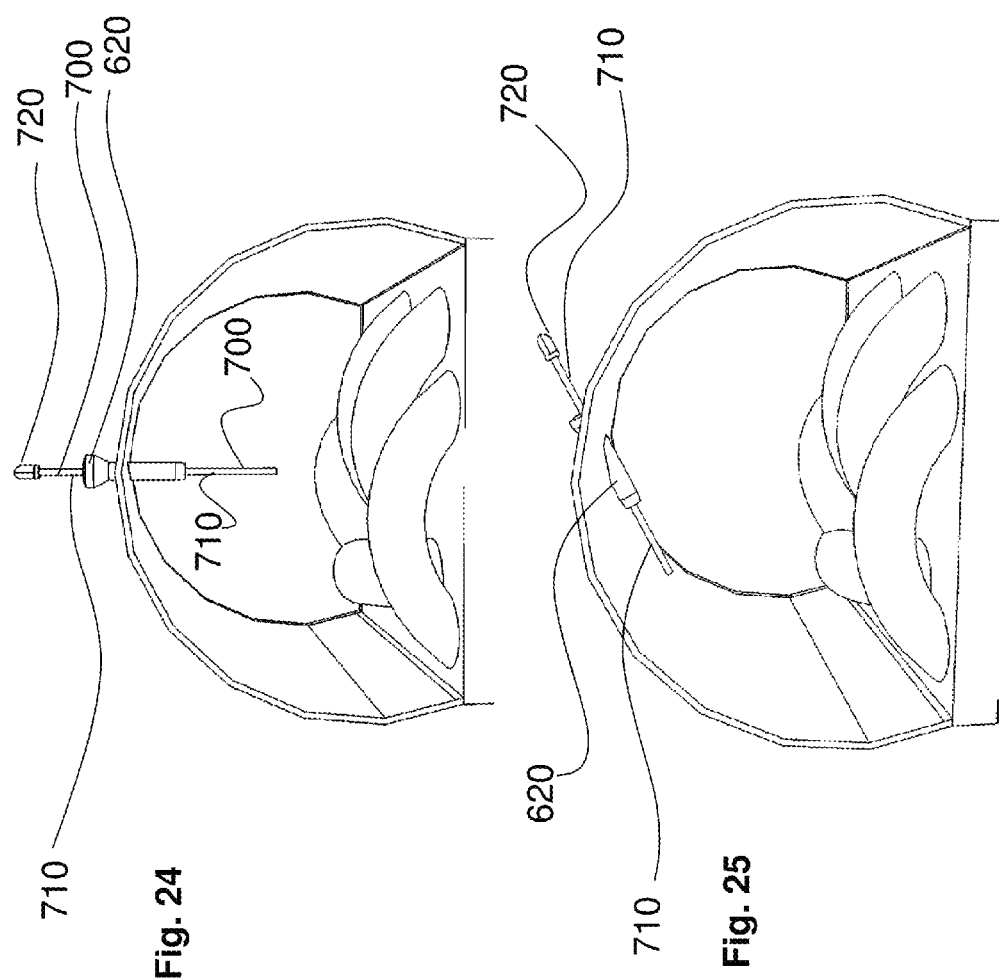

FIG. 24 shows an operating tool 700 with a wide head 720 and a narrow shaft 710 being inserted through a trocar 620 into a body cavity. Note that in the figure the wide operating-tool head 720 is positioned outside the body, and the narrow shaft 710 is inserted through the trocar into that body. If FIG. 25 the trocar, and the tool within it, is seen to be oriented so that the narrow shaft of the tool is aimed towards a selected portion of the outer wall of the body cavity.

Figure 26:
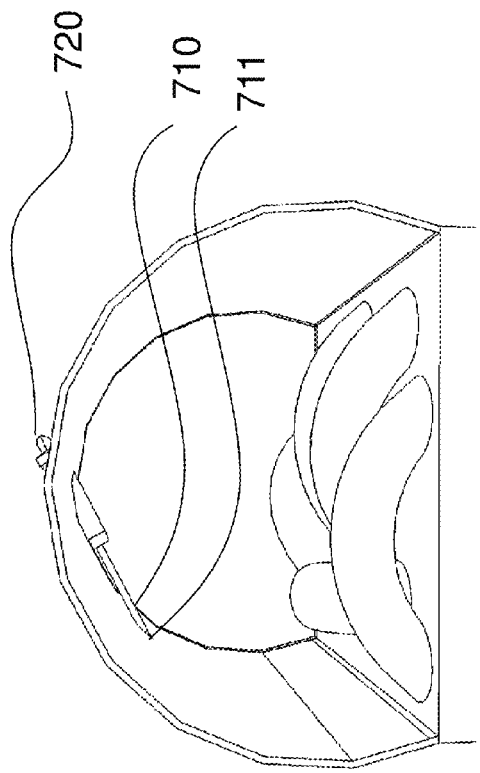
Figure 27:
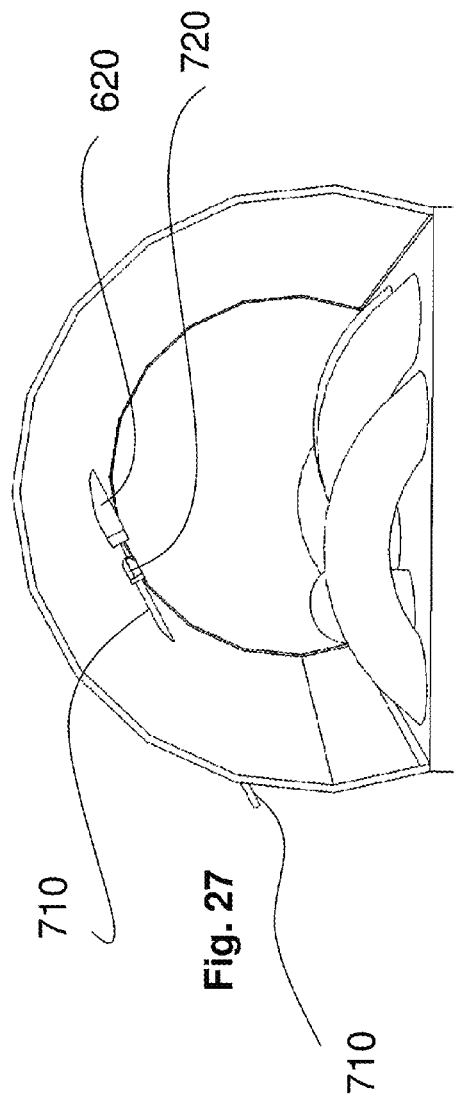

FIG. 26 shows the shaft (which may have a sharp end 711) starting to puncture the cavity wall, moving from inside the body cavity towards the outside. A continuation of the process is shown in FIG. 27, in which the shaft has penetrated the cavity wall, and can be grasped from outside the patient's body. The shaft can then be draw sufficiently far outside the patient's body so that the opposite end of the tool, with operating head attached, can be drawn through the trocar and into the body cavity. In the situation shown in FIG. 28, the operating head and distal portion of the tool are within the body cavity, and the tool's shaft is outside the body cavity. FIG. 29 shows a handle 300 attached to the tool, which is now read for surgical work within the body cavity. It the series of figures now described only one tool has been so inserted, but it is to be understood that a plurality of tools may be inserted into the body cavity in this manner, each having only a narrow-diameter puncture penetration of the body cavity wall and a wide operating tool head.

An optional additional embodiment is shown in FIG. 30, where a narrow trocar 740, only slightly larger than the diameter of the tool shaft 710, is positioned on the tool shaft prior to connection of handle 300 to shaft. The trocar can be slid down the shaft and into the puncture hole around the shaft, where it serves to facilitate free motion of the shaft during the surgical procedure and also serves to preserve gas pressure within the body cavity if the body cavity is inflated, as is often the case during surgical procedures.

Attention is now drawn to FIGS. 31-39, which present aspects of a surgical procedure whereby a treatment tool with narrow shaft and relatively wide treatment head can be introduced into a body cavity and manipulated through a narrow incision.

FIG. 31 shows a surgical tool 700 partially introduced through a trocar into a body cavity, with shaft 710 in the body cavity and operating head 720 outside the cavity. A handle 301 which comprises an internal stiffener 370 having a sharp point 372 is shown inserted in the handle 301, outside the body. (The stiffener is shown in dark color)

Figure 33:
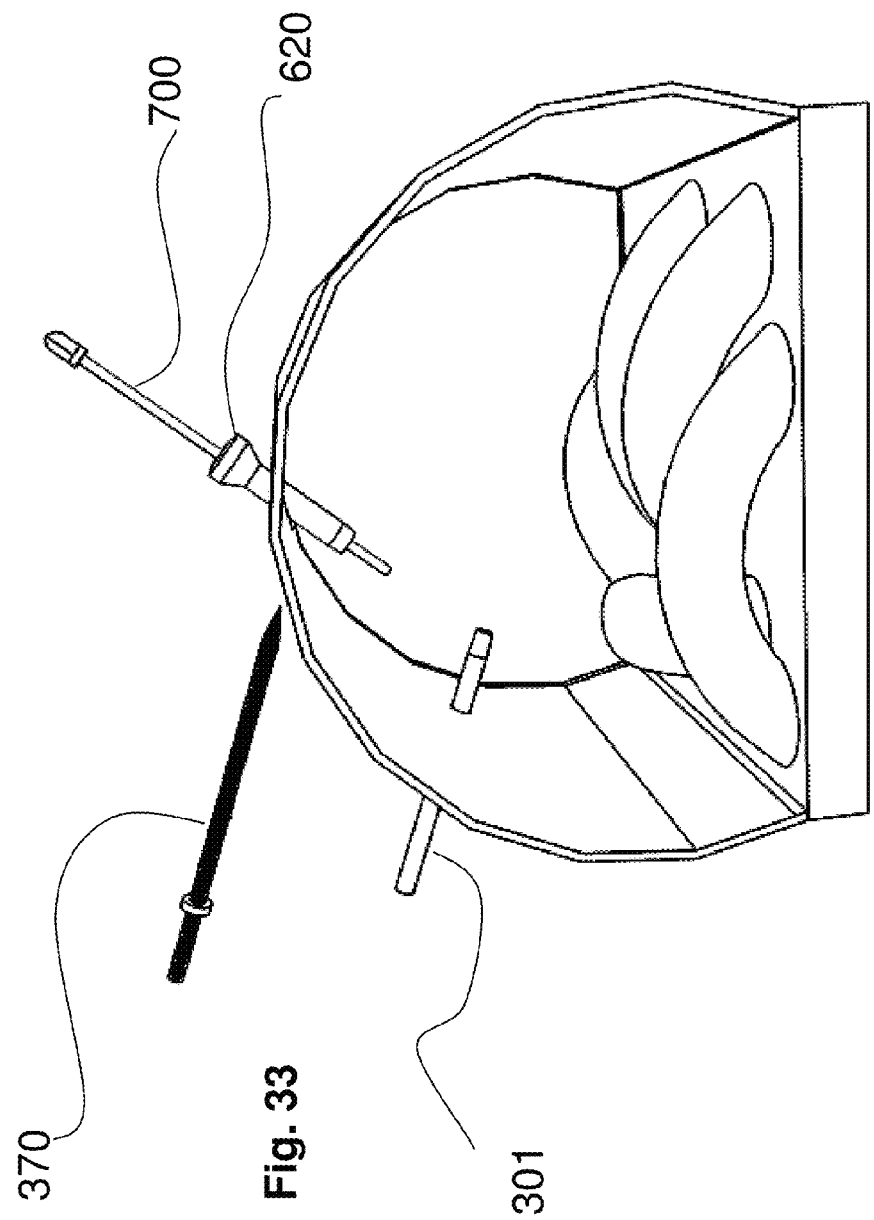

FIG. 32 shows the handle 301, with stiffener inserted, penetrating into the body cavity wall. In FIG. 33 the stiffener 370 has been removed, the handle 301 remains penetrating the cavity wall. In FIG. 34, the shaft 710 of the tool 700 inserted through the trocar, and the handle 301 inserted through the cavity wall are oriented towards each other, in FIG. 35 they approach each other and in FIG. 36 they connect. Shaft and handle are provided with a connecting mechanism 725 such as matching screw threads (103, 104) or any other attaching mechanism. A surgeon, manipulating both tools by their portions positioned outside the body, can connect them.

Once handle and tool are connect, the handle can be partially retracted from the body, pulling the operating tool head through the trocar and into the body cavity, as shown in FIG. 37. In FIG. 38 the tool is shown with operating head within the body cavity and free to move, it's handle being outside the body where it can be manipulated by a surgeon. FIG. 39 shows the tool approaching a surgical intervention site within the body cavity.

To remove the tool, the surgeon can use the handle to insert the operating head of the tool into the trocar, where he can grasp it from outside the body, and unscrew it or otherwise disconnect it from the handle. Thereafter both the tool and the handle can be removed from the body. The procedure can be used in introduce a plurality of such tools through a single trocar, enabling a surgeon to employ a plurality of tools with wide heads without needing a plurality of wide openings in the body cavity wall.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of surgery which comprises:
   inserting a trocar into a body cavity;
   passing a shaft of a surgical tool through a wall of a body cavity through an incision not substantially larger than a diameter of said shaft and distant from said trocar, so that a proximal portion of said shaft is external to said cavity and a distal portion of said shaft is internal to said cavity;
   passing the distal portion of said shaft from within said body cavity through said trocar until said distal portion emerges from said body cavity, and there attaching an operating tool head to said shaft while said distal shaft portion is outside the body, then retracting said shaft and operating tool head entirely through said trocar to position said attached operating tool head entirely within said cavity, and
   using a portion of said shaft external to said body cavity to manipulate said operating tool head within said cavity during a surgical procedure.

2. A method for attaching an operating tool to a shaft of a laparoscopic tool at least a portion of which is inserted in a body, comprising:
   passing a distal end of a shaft of said laparoscopic tool from within a body cavity through a trocar installed in a wall of said body cavity to a position where said distal end is outside the body and a portion of said shaft is still within said body cavity;
   then attaching said operating tool to said shaft distal end while said tool and said shaft distal end are both outside the body; and
   then retracting said shaft distal end, with tool attached, back through said trocar into said body cavity.

3. The method of claim 2, further comprising removing said attached tool from said shaft by passing said tool from inside said body cavity through said trocar to a position outside said body, and there disconnecting said tool from said shaft distal portion.

4. The method of claim 2, wherein width of said head is greater than a width of said shaft.

5. The method of claim 2, wherein said shaft comprises a distal connecting mechanism for connecting to said operating head and a lumen for a moveable control element attachable to said head.

6. A method for positioning a laparoscopic tool for a surgical operation within a body cavity, comprising:
   installing a first trocar at a first position in a wall of a body cavity;
   introducing shaft-first into said first trocar a laparoscopic tool having a wide operating head on a proximal first end of a shaft and a distal second end of said shaft, the distal second end being introduced before the proximal first end;
   extending said shaft from inside said body cavity to a second position at the wall of said cavity, and causing the distal second end of said shaft to extend beyond said body cavity;
   handling the distal second end of said shaft which has extended beyond said cavity to draw the proximal first end of said shaft and said operating head entirely into said body cavity through said first trocar; and
   using the distal second end of said shaft which is extended beyond said body cavity to manipulate, from outside said body cavity, said head which is positioned within said body cavity,
   wherein the distal second end of said shaft is sharp, and penetrates said wall to extend said shaft distal second end beyond said body cavity.

7. The method of claim 6, wherein said shaft is narrower in diameter than said operating head.

8. The method of claim 6, further comprising attaching a handle to said shaft at the distal second end extending beyond said body cavity.

9. The method of claim 6, further comprising sliding a second trocar along said shaft past the second distal end extending beyond said body cavity until the second trocar enters a puncture incision created by said sharp distal second end of said shaft.

10. The method of claim 9, wherein a diameter of said second trocar is only slightly larger than a diameter of said shaft.

11. A method for positioning a laparoscopic tool for a surgical operation within a body cavity, said laparoscopic tool comprising an operating head, a shaft, and a handle, comprising:
   installing a trocar in a wall of a body cavity;
   introducing into said trocar a laparoscopic tool which has an operating head on a first end of a shaft and a connecting mechanism on a second end of said shaft, said introducing being shaft-first, so that said head is initially outside said body cavity while said second end of said shaft is inserted through said trocar into said body cavity;
   penetrating said body cavity with a distal portion of said handle, so that a proximal portion of said handle is outside said body cavity and a distal portion of said handle is within said body cavity;
   connecting said distal portion of said handle to said second end of said shaft inside said body cavity; and
   using said proximal portion of said handle to draw said operating head into said body cavity through said trocar.

\* \* \* \* \*